(12) United States Patent
Akashi et al.

(10) Patent No.: US 12,203,062 B2
(45) Date of Patent: Jan. 21, 2025

(54) CELL CHIP AND THREE-DIMENSIONAL TISSUE CHIP, AND METHOD FOR PRODUCING SAME

(71) Applicants: OSAKA UNIVERSITY, Osaka (JP); NTN CORPORATION, Osaka (JP)

(72) Inventors: Mitsuru Akashi, Suita (JP); Takami Akagi, Suita (JP); Masaki Egami, Iwata (JP); Akihiro Yamanaka, Iwata (JP); Haruka Nakamura, Iwata (JP); Toukokuryuu Ai, Iwata (JP)

(73) Assignees: OSAKA UNIVERSITY, Osaka (JP); NTN CORPORATION, Osaka (JP)

( * ) Notice: Subject to any disclaimer, the term of this patent is extended or adjusted under 35 U.S.C. 154(b) by 1073 days.

(21) Appl. No.: 16/760,087

(22) PCT Filed: Nov. 1, 2018

(86) PCT No.: PCT/JP2018/040715
§ 371 (c)(1),
(2) Date: Apr. 29, 2020

(87) PCT Pub. No.: WO2019/088224
PCT Pub. Date: May 9, 2019

(65) Prior Publication Data
US 2020/0263119 A1 Aug. 20, 2020

(30) Foreign Application Priority Data
Nov. 2, 2017 (JP) .................. 2017-213095

(51) Int. Cl.
| | | |
|---|---|---|
| *C12N 5/00* | (2006.01) | |
| *B01L 3/00* | (2006.01) | |
| *C12M 1/00* | (2006.01) | |
| *C12M 1/12* | (2006.01) | |
| *C12M 1/26* | (2006.01) | |
| *C12M 1/32* | (2006.01) | |

(52) U.S. Cl.
CPC ....... *C12M 25/14* (2013.01); *B01L 3/502753* (2013.01); *C12M 23/12* (2013.01); *C12M 29/00* (2013.01); *C12M 33/04* (2013.01); *C12N 5/0062* (2013.01); *C12N 5/0068* (2013.01); *B01L 2300/0829* (2013.01)

(58) Field of Classification Search
None
See application file for complete search history.

(56) References Cited

U.S. PATENT DOCUMENTS

| | | |
|---|---|---|
| 2011/0129892 A1 | 6/2011 | Umezu et al. |
| 2017/0267975 A1 | 9/2017 | Hasegawa et al. |
| 2018/0126343 A1* | 5/2018 | Wiles .............. C12M 33/04 |

FOREIGN PATENT DOCUMENTS

| | | |
|---|---|---|
| EP | 1 243 327 | 9/2002 |
| JP | 2008-17798 | 1/2008 |
| JP | 2008-126459 | 6/2008 |
| JP | 2010-22251 | 2/2010 |
| JP | 2010-98958 | 5/2010 |
| JP | 2011-155865 | 8/2011 |
| JP | 2015-229148 | 12/2015 |
| JP | 2016-59909 | 4/2016 |
| JP | 2016-87822 | 5/2016 |
| JP | 2017-131144 | 8/2017 |
| JP | 2017-163931 | 9/2017 |
| JP | 2017-169560 | 9/2017 |
| WO | 2015/025957 | 2/2015 |
| WO | 2016/047423 | 3/2016 |
| WO | 2016/164712 | 10/2016 |

OTHER PUBLICATIONS

Johnson et al. 3D printed nervous system on a chip, (2016), Lab Chip, pp. 1393-1400 (Year: 2016).*
Office Action issued Sep. 27, 2022 in corresponding Japanese Patent Application No. 2019-235027, with English-language translation.
Dennis, Sarah Grace et al., "Viability of Bioprinted Cellular Constructs Using a Three Dispenser Cartesian Printer", Journal of Visualized Experiments, Sep. 2015, vol. 103, No. e53156, pp. 1-12.
International Search Report (ISR) issued Jan. 29, 2019 in International (PCT) Application No. PCT/JP2018/040715.
Extended European Search Report issued Jul. 2, 2021 in corresponding European Patent Application No. 18872417.3.
Kim, J. et al. "Direct-Write Patterning of Bacterial Cells by Dip-Pen Nanolithography" Journal of the American Chemical Society, Oct. 10, 2012, vol. 134, No. 40, pp. 16500-16503, XP055817266.
J. V. I. Timonen et al., "Trapping, manipulation, and crystallization of live cells using magnetofluidic tweezers", Nanoscale Horizons, Oct. 3, 2016, vol. 2, No. 1, 3, pp. 50-54, XP055817131.
T. Brandstetter, "Biochip Technologies Biochip-Technologies Content", Apr. 26, 2013, XP055817370.
Chikae, Shohei et al., "Three-dimensional bioprinting human cardiac tissue chips of using a painting needle method" Biotechnology and Bioengineering, vol. 116, No. 11, Aug. 1, 2019, pp. 3136-3142, XP055817148.

* cited by examiner

*Primary Examiner* — Teresa E Knight
(74) *Attorney, Agent, or Firm* — Wenderoth, Lind & Ponack, L.L.P.

(57) ABSTRACT

The present invention is to provide a cell chip and a three-dimensional tissue chip and a production method therefor such that even when a highly viscous cell-containing solution is a material, the highly safe and reproducible cell chip or three-dimensional tissue chip with a desired application volume can be produced within a short time and in a large quantity so as to have a desired cell density and exhibit high cell viability.

23 Claims, 19 Drawing Sheets

(a)

(b)

(c)

(a)

(b)

(c)

(a)

(b)

(c)

(a)

(b)

CELL CHIP AND THREE-DIMENSIONAL TISSUE CHIP, AND METHOD FOR PRODUCING SAME

TECHNICAL FIELD

The present invention relates to an ex vivo cell chip or three-dimensional tissue chip, and a production method therefor.

BACKGROUND ART

Technology for ex vivo cellular three-dimensional tissue construction is critical in research on drug discovery and regenerative medicine. Human biological tissue-resembling cellular tissue construction, in particular, has been sought.

In the case of ex vivo cell manipulation, it is common to culture cells two-dimensionally by using cultureware, such as a plastic or glass dish. However, cells actually proliferate in vivo three-dimensionally to form a tissue or organ. Thus, in order to realize in vivo resembling culture conditions, it is critical for progression in drug discovery research and regenerative medicine research to construct a three-dimensional cell/tissue chip and use the three-dimensional tissue chip for evaluation and experiment.

Each three-dimensional tissue chip (cell assembly), on which cells assemble and aggregate to one another, is placed on, for instance, each well (recessed portion) aligned on a well plate to evaluate each cell assembly. This assay has been widely used in evaluation of cellular function and screening for a compound effective as a novel pharmaceutical. Such cell assemblies may be assayed to evaluate many items within a short time by using a small amount of sample. This is advantageous from the viewpoint of making the evaluation rapid, simple, safe, reproducible, and highly reliable.

Examples of technology for precisely patterning cells on a substrate include a method of processing a substrate using a photolithography technique for controlling cell adhesion and a method of directly printing cells for arrangement and immobilization. Recently, 3D printer technology for three-dimensionally (3D) arranging and layering cells has advanced and cell assembly construction using a 3D printer has been investigated. Here, it has considerably been developed to apply a tissue model obtained from cell assemblies to drug discovery research and regenerative medicine.

CITATION LIST

Patent Literature

[Patent Literature 1] JP 2008-126459 A
[Patent Literature 2] JP 2008-017798 A
[Patent Literature 3] JP 2010-022251 A
[Patent Literature 4] JP 2015-229148 A
[Patent Literature 5] JP 2016-087822 A
[Patent Literature 6] JP 2017-163931 A
[Patent Literature 7] JP 2017-169560 A
[Patent Literature 8] JP 2017-131144 A

SUMMARY OF INVENTION

Technical Problem

As the 3D printer for cell assembly construction, there are an inkjet printer (inkjet type: a thermal type, piezoelectric type), a microextrusion printer (of dispenser type), and a laser-assisted printer (of pulse laser type). Unfortunately, in these printers, a dischargeable material is limited and their printing rate (production rate) and resolution (discharge volume) have also been restricted. Further, when the material to be discharged is a cell-containing solution containing cells, conventional 3D printers have had problems with a cell assembly to be produced regarding, for instance, the cell viability and the cell density after discharged. In the case of producing a cell assembly from a highly viscous cell-containing solution, in particular, there is a risk of clogging of highly viscous solution in a printer nozzle. Thus, it is impossible to provide a high resolution, that is, to produce fine cell assemblies in a large quantity, which has been a problem.

The purpose of the present invention is to provide a cell chip and a three-dimensional tissue chip and a production method therefor such that the cell chip or three-dimensional tissue chip with a desired application volume can be produced within a short time (at a high speed) and in a large quantity even if a highly viscous cell-containing solution is a material and the produced cell chip or three-dimensional tissue chip has a desired cell density so as to exhibit high cell viability.

Solution to Problem

To achieve the goal, a method for producing a cell chip or three-dimensional tissue chip according to an aspect of the invention includes:
  an attachment step of attaching a cell-containing solution to a tip of an application needle;
  a transfer step of moving the cell-containing solution-attached tip of the application needle closer to an application target;
  an application step of bringing the cell-containing solution attached to the tip of the application needle into contact with the application target or into contact with the cell-containing solution having already been applied on the application target, thereby subjecting the cell-containing solution attached to the tip of the application needle to contact application; and
  a separation step of, after the cell-containing solution is subjected to the contact application, making the tip of the application needle apart from the application target.

In addition, to achieve the goal, a method for producing a cell chip or three-dimensional tissue chip according to an aspect of the invention by using a micro-applicator provided with an application unit including an application liquid container having an application liquid reservoir for storing a cell-containing solution in a prescribed amount and an application needle allowing for penetration through the application liquid reservoir having the cell-containing solution stored, the method including:
  a waiting step of making a tip of the application needle dipped into the cell-containing solution having been charged in the application liquid reservoir;
  a descending step of making the tip of the application needle penetrate through the application liquid reservoir to move downward the cell-containing solution-attached tip of the application needle;
  an application step of bringing the cell-containing solution-attached tip of the application needle into contact with an application target, thereby applying the cell-containing solution to the application target to form a liquid droplet spot; and a holding step of lifting the tip of the application needle and holding the tip of the application needle in the application liquid reservoir.

Further, to achieve the goal, a cell chip or three-dimensional tissue chip according to an aspect of the invention is produced by at least the cell chip or three-dimensional tissue chip production method.

Advantageous Effects of Invention

According to the invention, a cell chip and a three-dimensional tissue chip with a desired application volume can be produced within a short time and in a large quantity even if a highly viscous cell-containing solution is a material and the produced cell chip or three-dimensional tissue chip has a desired cell density so as to exhibit high cell viability.

DESCRIPTION OF EMBODIMENTS

Figure 1:
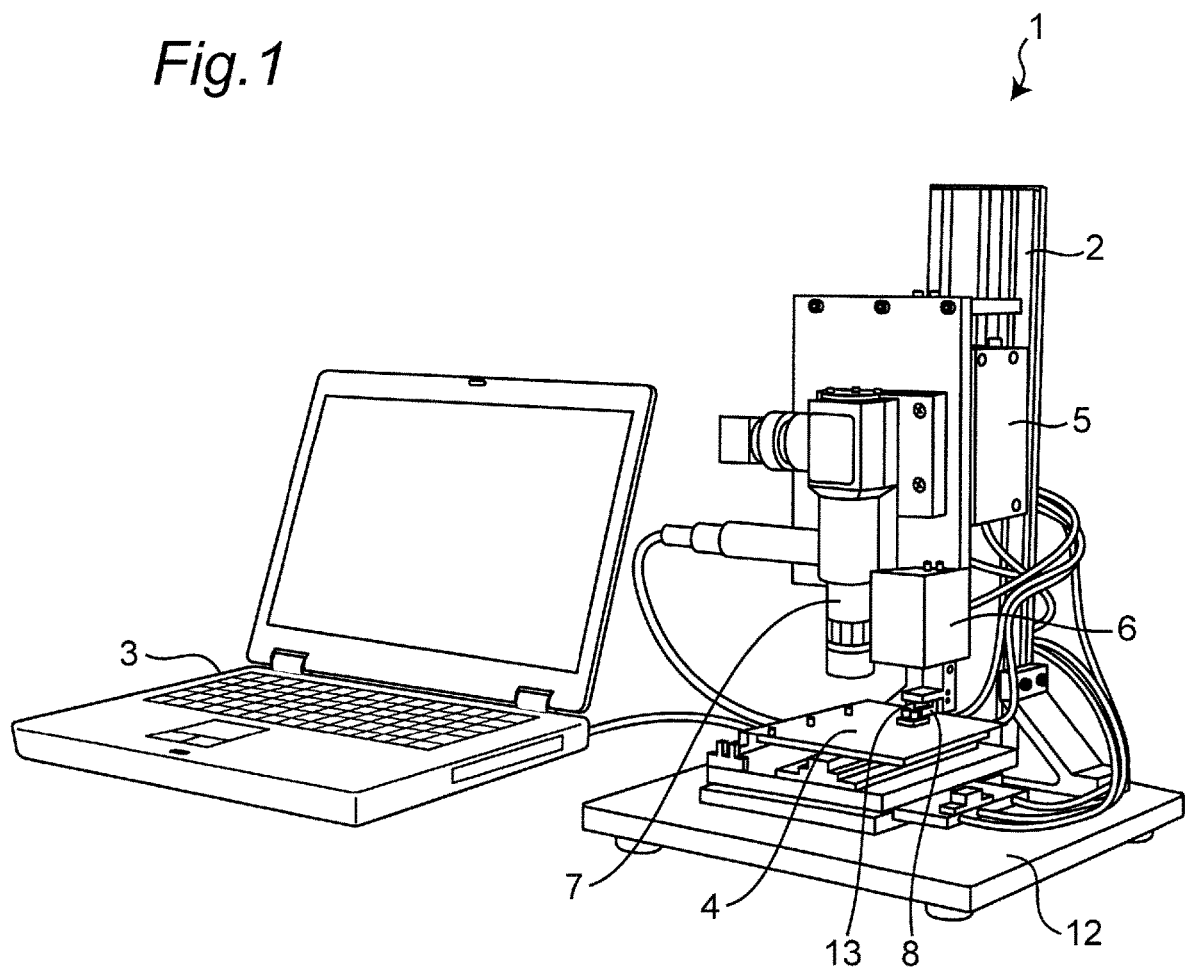
FIG. 1 is a diagram illustrating a whole micro-applicator used in a first embodiment according to the invention.

First, various aspects in a cell chip or three-dimensional tissue chip production method according to the invention are described. Note that the cell chip in the invention refers to a chip in a state in which individual cells are substantially dispersed and adhered on, for instance, a substrate. The three-dimensional tissue chip refers to a cell assembly in a state in which cells are assembled, aggregated, and layered on a substrate to form a three-dimensional tissue and are functioning. Here, any shape of the cell assembly, such as a spherical shape or a flat shape, is acceptable.

A method for producing a cell chip or three-dimensional tissue chip according to a first aspect according to the invention is characterized by including:
  an attachment step of attaching a cell-containing solution to a tip of an application needle;
  a transfer step of moving the cell-containing solution-attached tip of the application needle closer to an application target;
  an application step of bringing the cell-containing solution attached to the tip of the application needle into contact with the application target or into contact with a cell-containing solution having already been applied on the application target, thereby subjecting the cell-containing solution attached to the tip of the application needle to contact application; and
  a separation step of, after the cell-containing solution is subjected to the contact application, making the tip of the application needle apart from the application target.

For a method for producing a cell chip or three-dimensional tissue chip according to a second aspect of the invention, multiple cycles of cell application operation may be repeated while one cycle of the cell application operation includes the attachment step, the transfer step, the application step, and the separation step in the first aspect.

A method for producing a cell chip or three-dimensional tissue chip according to a third aspect of the invention by using a micro-applicator provided with an application unit including an application liquid container having an application liquid reservoir for storing a cell-containing solution in a prescribed amount and an application needle allowing for penetration through the application liquid reservoir having the cell-containing solution stored includes:
- a waiting step of making a tip of the application needle dipped into the cell-containing solution having been charged in the application liquid reservoir;
- a descending step of making the tip of the application needle penetrate through the application liquid reservoir to move downward the cell-containing solution-attached tip of the application needle;
- an application step of bringing the cell-containing solution-attached tip of the application needle into contact with an application target, thereby applying the cell-containing solution to the application target to form a liquid droplet spot; and
- a holding step of lifting the tip of the application needle and holding the tip of the application needle in the application liquid reservoir.

For a method for producing a cell chip or three-dimensional tissue chip according to a fourth aspect of the invention, multiple cycles of cell application operation may be repeated while one cycle of the cell application operation includes the waiting step, the descending step, the application step, and the holding step performed with respect to certain positions relative to the application target in the third aspect.

For a method for producing a cell chip or three-dimensional tissue chip according to a fifth aspect of the invention, one cycle of the cell application operation may be conducted in 0.5 sec or shorter in the second or fourth aspect.

For a method for producing a cell chip or three-dimensional tissue chip according to a sixth aspect of the invention, the cell application operation may be carried out using a material in which the viscosity of the cell-containing solution is $1\times10^5$ mPa·s or less and preferably from 1 to $1\times10^4$ mPa·s in any one of the second, fourth, or fifth aspect.

For a method for producing a cell chip or three-dimensional tissue chip according to a seventh aspect of the invention, a liquid droplet spot obtained by the one cycle of the cell application operation may be formed with positional precision of ±15 μm or less with respect to the application target in any one of the second, fourth, fifth, or sixth aspect.

For a method for producing a cell chip or three-dimensional tissue chip according to an eighth aspect of the invention, a liquid droplet spot obtained by the one cycle of the cell application operation may be formed with positional precision of ±3 μm or less with respect to the application target in any one of the second, fourth, fifth, or sixth aspect.

For a method for producing a cell chip or three-dimensional tissue chip according to a ninth aspect of the invention, multiple cycles of the cell application operation may be repeated while a stop position of the tip of the application needle in the application step is shifted upward with respect to a certain position relative to the application target by a given distance every cycle of the cell application operation in any one of the second, fourth, fifth, sixth, seventh, or eighth aspect.

For a method for producing a cell chip or three-dimensional tissue chip according to a tenth aspect of the invention, the application unit may include a sliding mechanism part for slidably holding the application needle in the third or fourth aspect.

For a method for producing a cell chip or three-dimensional tissue chip according to an eleventh aspect of the invention, the sliding mechanism part may have a mechanism for absorbing a shock when the tip of the application needle comes into contact with the application target in the tenth aspect.

For a method for producing a cell chip or three-dimensional tissue chip according to a twelfth aspect of the invention, the tip of the application needle may be configured to move in a vertical direction during the application step of any one of the first to eleventh aspects.

For a method for producing a cell chip or three-dimensional tissue chip according to a thirteenth aspect of the invention, the tip of the application needle may include a flat surface perpendicular to a transfer direction of the application needle during the application step in any one of the first to twelfth aspects.

For a method for producing a cell chip or three-dimensional tissue chip according to a fourteenth aspect of the invention, the tip of the application needle may include a recessed surface in any one of the first to thirteenth aspects.

For a method for producing a cell chip or three-dimensional tissue chip according to a fifteenth aspect of the invention, it is possible to use, as a cell(s) in the cell-containing solution, a cell(s) having a cell surface coated with, for instance, an extracellular matrix protein, a sugar chain, and/or a natural or synthetic polymer so as to increase inter-cellular adhesion in any one of the first to fourteenth aspects.

A cell chip or three-dimensional tissue chip according to a sixteenth aspect of the invention is a cell chip or three-dimensional tissue chip produced by the method for producing a cell chip or three-dimensional tissue chip according to any one of the first to fifteenth aspects.

In the methods for producing a cell chip or three-dimensional tissue chip according to the invention, as described using specific examples in the below-described embodiments, a micro-applicator is used which can be utilized to highly precisely apply several pL (picoliter) of a tiny liquid droplet attached to the tip of an application needle to a predetermined position on a target within a very short time, such as 0.1 sec, per application. This allows for increased safety and reproducibility and automation. Thus, it is presented to produce a highly reliable cell chip or three-dimensional tissue chip (cell assembly) within a short time and in a large quantity.

The invention makes it possible to produce, with high precision, a plurality of three-dimensional tissue chips (cell assemblies) by using a high-speed micro-applicator to reliably apply, onto a predetermined position within a short time, a highly viscous (50 mPa·s or higher) material, such as a highly viscous solution containing cells and a gelatinizer, which has not been successfully handled using any conventional printer. As a result, the invention makes it possible to optionally control and arrange desired cells two-dimensionally and three-dimensionally. Thus, various three-dimensional tissue chips can be produced under an aseptic condition and in a large quantity while the production is automated. Hence, the methods for producing a cell chip or three-dimensional tissue chip according to the invention make it possible to produce, in a large quantity by automation, a cell chip or three-dimensional tissue chip having increased safety and reproducibility and reliability.

Next, the methods for producing a cell chip or three-dimensional tissue chip according to the invention will be described, using embodiments representing specific configuration examples, by referring to the Drawings attached. Note that the methods for producing a cell chip or three-dimensional tissue chip according to the invention are not limited to configurations using micro-applicators in the below-described embodiments. The methods can be implemented by cell application operation (cell application method) in the technical ideas comparable to those for the cell application operation (cell application method) carried out in micro-applicators.

First Embodiment

Hereinafter, the first embodiment will be specifically described with reference to the Drawings attached. FIG. 1 is a diagram illustrating the whole micro-applicator 1 used in the first embodiment. As shown in FIG. 1, the micro-applicator 1 is provided with an applicator main body 2 and a display/control unit 3 configured to display, control, and set the applicator main body 2. What is called a personal computer (PC) is a component of the display/control unit 3 of the micro-applicator 1 in the first embodiment.

The applicator main body 2 of the micro-applicator 1 includes: an XY table 4 movable over a main body base 12 in a horizontal direction; a Z table 5 movable in a top-to-bottom direction (vertical direction) with respect to the XY table 4; an application unit 6 fixed to a driving mechanism movable, like the Z table 5, in the top-to-bottom direction; and an optical detection unit (e.g., a CCD camera) 7 configured to observe an application target on the XY table 4. For instance, a substrate, on which application liquid 10, a cell-containing solution, is applied to form a plurality of cell chips or three-dimensional tissue chips, is placed on and fixed to the XY table 4.

The application unit 6 in the micro-applicator 1 as so structured is configured to carry out cell application operation for aligning and forming a plurality of cell chips or three-dimensional tissue chips on, for instance, a substrate over the XY table 4. Hereinbelow, the structure of the application unit 6 and the cell application operation by using the application unit 6 will be described.

[Structure of Application Unit]

Figure 2:
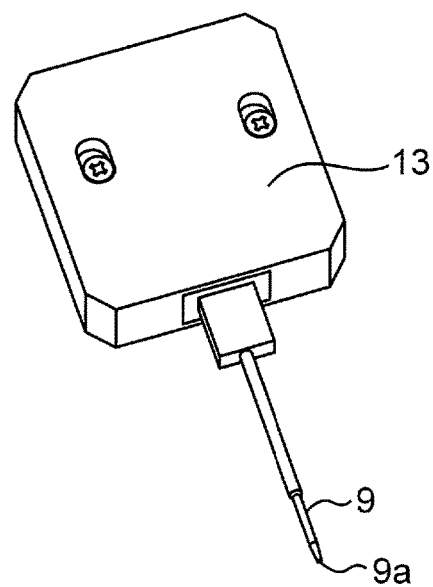
FIG. 2 is a diagram illustrating an application needle holder part mounted on an application unit in the micro-applicator.
Figure 3:
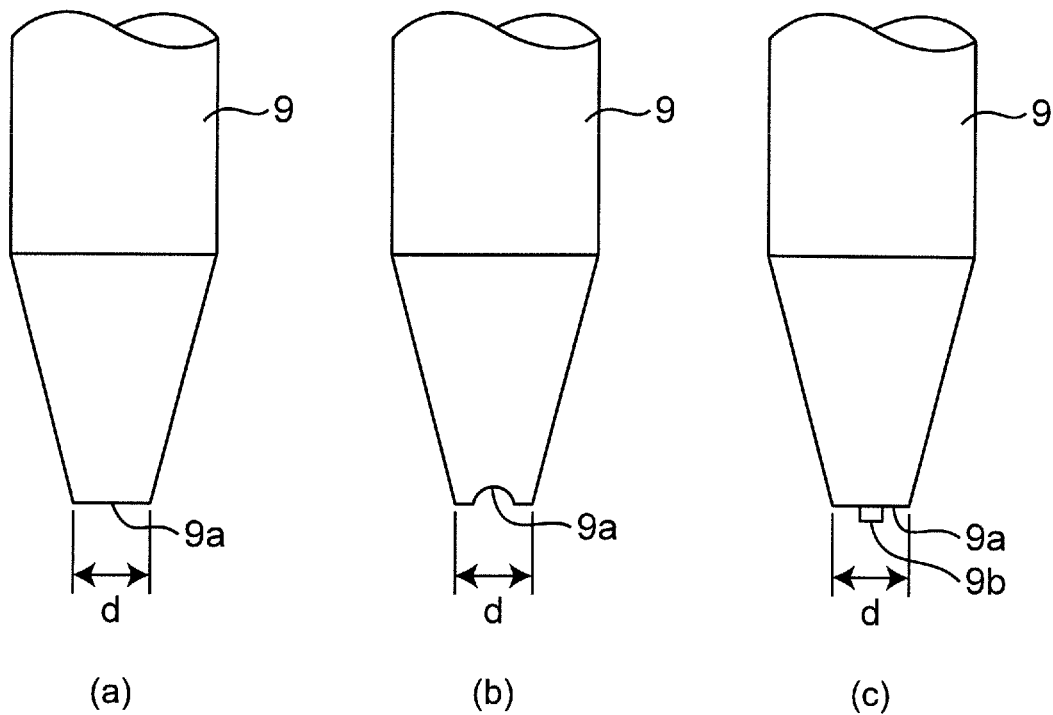
FIG. 3 is a diagram showing tip portions of application needles provided to the application needle holder part.

FIG. 2 is a diagram illustrating an application needle holder part 13 mounted on the application unit 6. An application needle 9 protrudes from the application needle holder part 13. FIG. 3 is diagrams illustrating a tip portion of each application needle 9. Regarding the application needle 9 in the first embodiment, a tip 9a of cone-shaped leading edge portion has a flat surface (is flat) so as to face a horizontal surface of the XY table 4 (see (a) of FIG. 3). That is, the flat surface of the tip 9a is a flat surface perpendicular to the vertical direction. The diameter d of the tip 9a substantially contributes to the shape of each cell chip or three-dimensional tissue chip to be produced, which will be described later. In the first embodiment, the tip 9a of the application needle 9 has a diameter d of from 50 to 330 μm. In the first embodiment, as shown in (a) of FIG. 3, the leading edge portion of the application needle 9 is shaped like a cone. The tip 9a has a horizontal surface. Accordingly, the tip 9a may be polished to a horizontal surface so as to easily adjust the diameter d of the tip 9a to a desired value ranging from, for instance, 50 to 330 μm.

Note that, in the first embodiment, the tip 9a of the application needle 9 is explained using an example of horizontal flat surface configuration (see (a) of FIG. 3). This tip 9a surface shape may have a recessed surface (semi-spherical surface) with a prescribed diameter, such as a diameter of 30 μm or less, and cells may be retained on the recessed surface so as to carry out cell application operation (see (b) of FIG. 3). Such formation of the tip 9a of the application needle 9 into a recessed surface makes it possible to produce a cell chip or three-dimensional tissue chip having a desired cell density and cell arrangement by the cell application operation using the application needle 9. In addition, as shown in (c) of FIG. 3, the tip 9a of the application needle 9 may have a stepped protrusion 9b. This configuration with such a protrusion 9b makes it possible to produce a cell assembly extending upward relative to a substrate by performing continuous and repeated application over the substrate while a needle tip is shifted upward by a given distance, such as 0.5 μm, every cell application operation.

Figure 4:
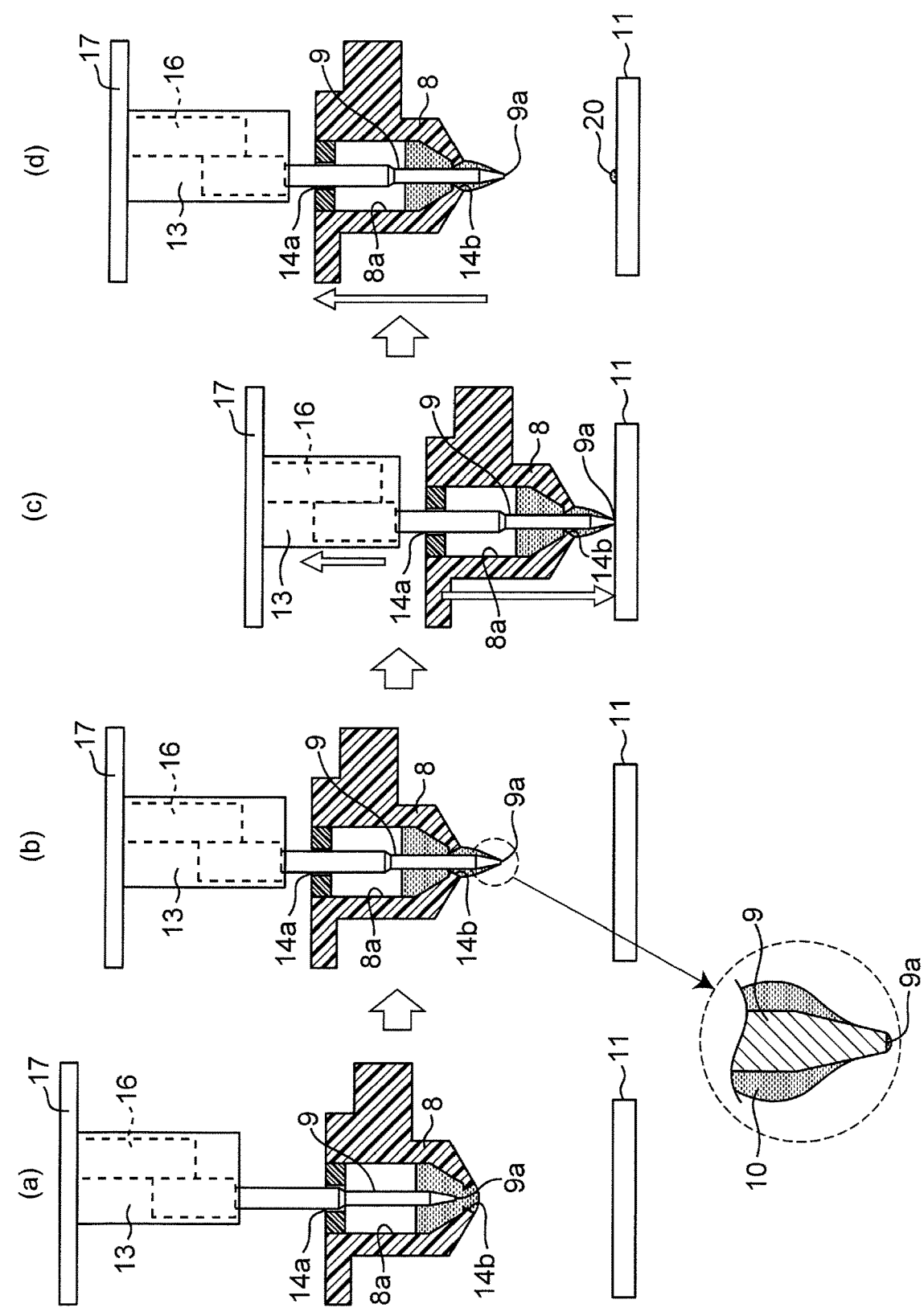
FIG. 4 is diagrams schematically illustrating cell application operation in the application unit.

FIG. 4 is diagrams schematically illustrating cell application operation in the application unit 6. As shown in FIG. 4, the application unit 6 includes: an application liquid container 8 having an application liquid reservoir 8a in which a prescribed amount of application liquid 10, a cell-containing solution, is stored; and the application needle holder part 13 equipped with the application needle 9 that penetrates through the application liquid reservoir 8a. The application needle holder part 13 is provided with a sliding mechanism part 16 that slidably holds the application needle 9 in the top-to-bottom direction (vertical direction). The application needle holder part 13 is detachably provided at a given position on a driving mechanism part 17, and, for instance, may be detachable from the driving mechanism part 17 by using magnetic force of a magnet.

The application needle holder part 13 is so fixed to the driving mechanism part 17 in the applicator main body 2 and is configured to reciprocally move between prescribed distances at a high speed in the top-to-bottom direction (vertical direction). The display/control unit 3 executes, for instance, settings of driving control of such a driving mechanism part 17 and driving control of the XY table 4 and the Z table 5. The sliding mechanism part 16 installed in the application needle holder part 13 can hold the vertically reciprocating application needle 9 and is configured to make the application needle 9 slide relative to the sliding mechanism part 16 in the vertical direction such that when coming into contact with a target, for instance, a substrate 11, the tip 9a of the application needle 9 stops at the contact position. That is, the sliding mechanism part 16 has a shock absorption mechanism when the application needle 9 comes into contact. Because of this, the tip 9a of the application needle 9 stops at the position in contact with an application target and is made apart from the application target in response to the subsequent upward movement of the driving mechanism part 17. Note that, the vertical reciprocating operation of the application needle 9 at that time is at an ultra-high speed. For instance, one reciprocating operation is set to preferably 0.5 sec or less and more preferably 0.1 sec or less.

As described above, the application needle holder part 13 in the application unit 6 is provided with the vertically slidable sliding mechanism part 16 while holding the application needle 9 and is detachably fixed to the vertically moving driving mechanism part 17. In addition, the application needle holder part 13 is configured such that the application needle 9 can move in the top-to-bottom direction (vertical direction) and penetrate through the application liquid reservoir 8a that stores the application liquid 10, a cell-containing solution. An upper portion and a lower portion of the application liquid container 8 each have a hole (upper hole 14a or lower hole 14b) through which the application needle 9 penetrates.

[Cell Application Operation]

Next, the cell application operation in the application unit 6, as schematically shown in FIG. 4, will be described. During the cell application operation illustrated in FIG. 4, the application needle 9 passes through the application liquid reservoir 8a of the application liquid container 8 and comes into contact with the substrate 11, which is an application target; and the cell-containing application liquid 10 is applied on the substrate 11 to form a liquid droplet spot S. This cell application operation is repeated prescribed times and the application liquid 10 is applied multiple times to produce a desired cell chip or three-dimensional tissue chip on the substrate 11. Note that in the first embodiment and other embodiments according to the invention, the substrate 11 is used, as an application target, for description. Here, the application target is not limited to a substrate and examples of the target include cultureware such as a plastic dish, a glass dish, or a well-plate commonly used for cell culture and/or various solutions on the cultureware.

(a) of FIG. 4 shows a waiting state during the cell application operation. In this waiting state, the application needle 9 is inserted from the upper hole 14a and the tip 9a of the application needle 9 is dipped into the application liquid 10 in the application liquid reservoir 8a. In such a waiting state (waiting step), the tip 9a of the application needle 9 is dipped into the application liquid 10, so that the application liquid 10 attached to the tip 9a is not dried. At that time, because the diameter of the lower hole 14b at the application liquid container 8 is very small (e.g., 1 mm or less), no leak of the application liquid 10 from the application liquid reservoir 8a occurs.

(b) of FIG. 4 shows a state (descending step) in which the tip 9a of the application needle 9 is projected from the lower hole 14b at the application liquid container 8 and the tip 9a descends toward the substrate 11 from the application liquid reservoir 8a. That is, (b) of FIG. 4 shows a descending state in which the tip 9a of the application needle 9 penetrates through and protrudes from the application liquid reservoir 8a of the application liquid container 8. During this descending state, the application liquid 10 is attached to the application needle 9 and the surface tension of the application liquid 10 attached causes the tip 9a of the application needle 9 to retain a certain volume of application liquid 10.

(c) of FIG. 4 shows a state (application step) in which the tip 9a of the application needle 9 comes into contact with a surface of the substrate 11 and the application liquid 10 is applied on the surface of the substrate 11. A liquid droplet spot S of the application liquid 10 applied at that time corresponds to a certain volume of application liquid 10 held on the tip 9a of the application needle 9. The first embodiment is configured such that an impact load at the moment when the tip 9a of the application needle 9 is in contact with (comes into contact with) a surface of the substrate 11 is about 0.06 N or lower. In the first embodiment, as described above, because the application needle 9 is slidably held by the sliding mechanism part 16 so as to absorb a vertical shock, the impact load at the time of contact is a very small value.

(d) of FIG. 4 shows a state immediately after the application needle 9 is used to apply the application liquid 10 on a surface of the substrate 11 and shows a state in which the application needle 9 is being lifted. This lifting state is followed by transition into a waiting state in which the tip 9a of the application needle 9 is dipped into the application liquid 10 of the application liquid reservoir 8a (holding step).

As described above, the one cycle of cell application operation includes, in sequence, (a), (b), (c), (d), and (a) operations as illustrated in FIG. 4. In the first embodiment, the one cycle of cell application operation is conducted in 0.1 sec, and the cell application operation is executed in a ultra-short period. Note that in the first embodiment, the cell application operation is repeated prescribed times (e.g., 10 cycles) to produce a desired cell chip or three-dimensional tissue chip. Meanwhile, 10 cycles of the application operation require 1 sec so as to produce 1 spot of three-dimensional tissue.

During the cell application operation using the micro-applicator 1 in the first embodiment according to the invention, the application needle 9 having a tip attached to a very small volume of application liquid 10 is brought into contact with an application target (e.g., the substrate 11); and a liquid droplet spot S in an application volume of several pL (picoliter) can be applied and formed with high positional precision, such as positional precision of ±15 μm or less and preferably ±3 μm or less. In addition, it is possible to apply a material with a viscosity of the application liquid 10 of $1 \times 10^5$ mPa·s or lower and preferably from 1 to $1 \times 10^4$ mPa·s. This allows for application of highly viscous cell dispersion. During the cell application operation using the micro-applicator 1 in the first embodiment, it is possible to use, as an application material, a material with a viscosity of from 10 mPa·s to $1 \times 10^5$ mPa·s (inclusive), which material has not been successfully used because nozzle-type printers such as inkjet printers have a problem of clogging, etc. In addition, the application needle 9 having a tip attached to a very small volume of application liquid 10 is brought into contact with an application target for application. Accordingly, the application is not affected by a variation in the vertical position of the application needle 9 and can be repeated using a desired application volume of application liquid 10 in a stable fashion. As such, in the first embodiment according to the invention, a highly viscous cell dispersion can be precisely applied at a predetermined position on, for instance, the substrate 11. This makes it possible to produce a cell chip with a given pattern or a three-dimensional tissue chip on which cells are shaped three-dimensionally. In view of the above, the method for producing a cell chip or three-dimensional tissue chip according to the invention exerts advantageous effects on progress in respective fields while the produced cell chip or three-dimensional tissue chip is utilized in the fields of regenerative medicine and drug discovery research such as drug efficacy or safety evaluation screening.

Experimental Example 1

The micro-applicator 1, which has been described in the above first embodiment, was used to conduct application experiment 1 using application liquids 10 with different concentrations and viscosities. In this application experiment 1, 3 different application liquids 10, including 5%, 10%, and 20% gelatin PBS (phosphate buffer solution) solutions, were used to examine the shape of each liquid droplet spot.

Three application liquid containers 8 in the application unit 6 were provided, and gelatin was dissolved at 5, 10, or 20% weight by volume (% w/v) in phosphate buffer solution (PBS) to prepare, as the application liquids 10, three different gelatin PBS solutions. Note that each application liquid 10 used in this application experiment 1 is free of cells.

In application experiment 1, each application liquid container 8 was filled with 20 μL of 5%, 10%, or 20% gelatin PBS solution. A needle having a tip 9a (flat surface shape) with a diameter d of 100 μm was used as the application needle 9 in the application unit 6. In this application experiment 1, each application liquid 10 was subjected to point contact and was applied as 5×5 spots with a 150-μm interval on a slide glass fixed to the XY table 4. The liquid droplet spots formed on the slide glass by the application were observed under a phase-contrast microscope.

Figure 5:
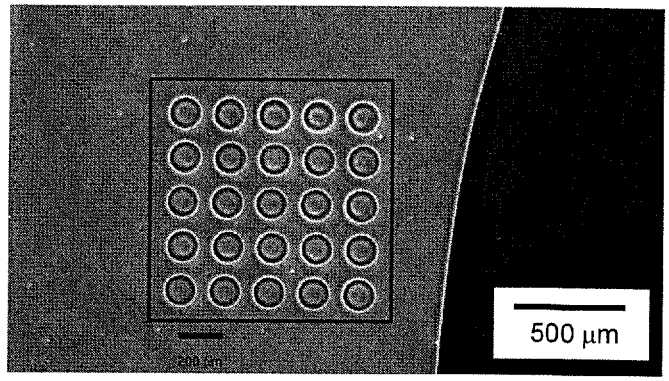
FIG. 5 is photographs showing images of liquid droplet spots observed under a phase-contrast microscope in application experiment 1.
Figure 5:
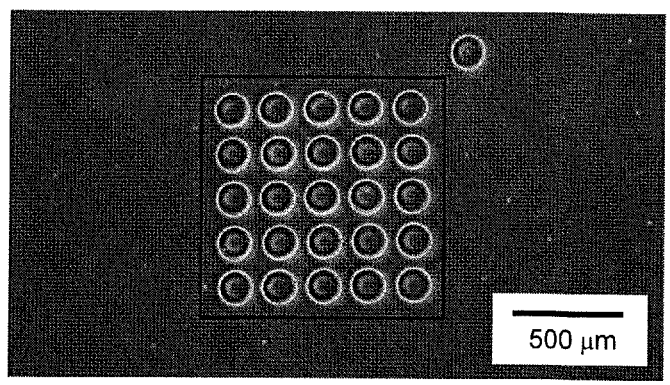
Figure 5:
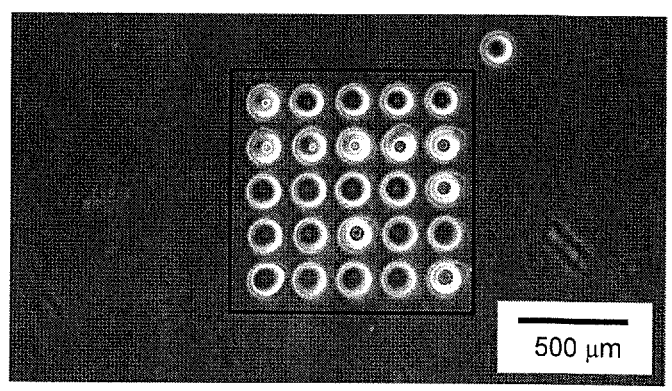

FIG. 5 is photographs showing images of the liquid droplet spots observed under a phase-contrast microscope in application experiment 1. (a) of FIG. 5 is an image showing liquid droplet spots formed by applying, as the application liquid 10, 5% gelatin PBS solution (with a viscosity of 3 mPa·s) on a slide glass by using an application needle 9 having a tip 9a with a diameter d (tip diameter) of 100 μm. (b) of FIG. 5 is an image showing liquid droplet spots formed by applying, as the application liquid 10, 10% gelatin PBS solution (with a viscosity of 30 mPa·s) on a slide glass by using the application needle 9 (with a tip diameter of 100 μm). In addition, (c) of FIG. 5 is an image showing liquid droplet spots formed by applying, as the application liquid 10, 20% gelatin PBS solution (with a viscosity of 220 mPa·s) on a slide glass by using the application needle 9 (with a tip diameter of 100 μm).

(a), (b), and (c) of FIG. 5 clearly demonstrate that when the application unit 6 of the micro-applicator 1 was used, the liquid droplet spots formed using the application liquids 10 even with different concentrations and viscosities had substantially the same shape (the 5% gelatin liquid droplet spots had a diameter of 136±3 μm, the 10% gelatin liquid droplet spots had a diameter of 147±1 μm, and the 20% gelatin liquid droplet spots had a diameter of 151±1 μm). That is, application experiment 1 successfully verified constantly stable liquid droplet spots, which did not significantly depend on the gelatin concentration and viscosity. According to the experiment conducted by the present inventors, the diameter of each liquid droplet spot was within a size 1.3 to 1.6 times the tip diameter of the application needle 9, and the liquid droplet was not at least twice as large as the tip diameter.

Experimental Example 2

The micro-applicator 1, which has been described in the above first embodiment, was used to conduct application experiment 2 using application needles 9 with different tip 9a diameters (tip diameters). In this application experiment 2, 5% gelatin PBS solution was used as the application liquid 10 to examine the shape of each liquid droplet spot formed. The application liquid 10 used in this application experiment 2 is free of cells.

In application experiment 2, three different application needles 9 having a tip diameter of 50 μm, 100 μm, or 150 μm were used. In application experiment 2, the application liquid 10 was subjected to point contact and was applied as 5×5 spots with a 150-μm interval on a slide glass fixed to the XY table 4. The liquid droplet spots formed on the slide glass by the application were observed under a phase-contrast microscope.

Figure 6:
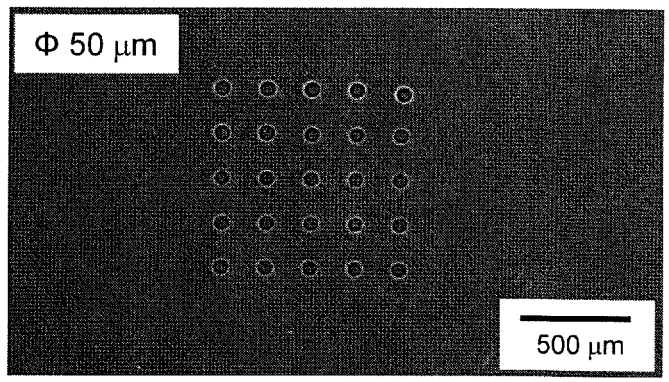
FIG. 6 is photographs showing images of liquid droplet spots observed under a phase-contrast microscope in application experiment 2.
Figure 6:
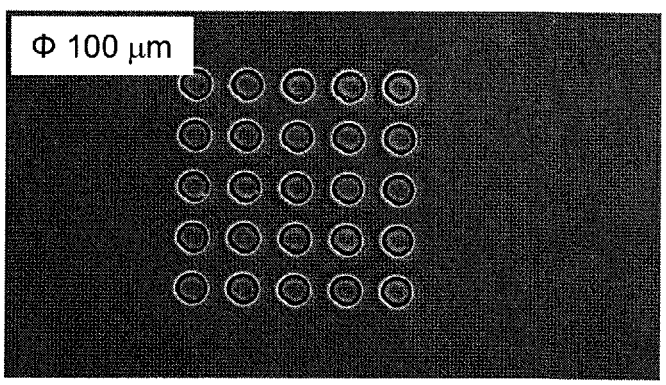
Figure 6:
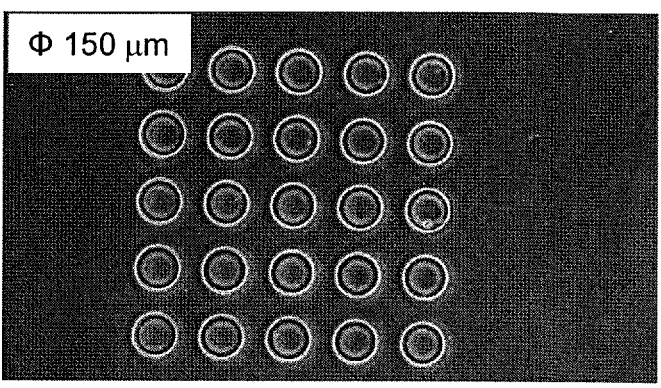

FIG. 6 is photographs showing images of the liquid droplet spots observed under a phase-contrast microscope in application experiment 2. (a) of FIG. 6 is an image showing liquid droplet spots formed by applying the application liquid 10 of 5% gelatin PBS solution on a slide glass by using an application needle 9 having a tip diameter of 50 μm. (b) of FIG. 6 is an image showing liquid droplet spots formed by applying the application liquid 10 of 5% gelatin PBS solution on a slide glass by using an application needle 9 having a tip diameter of 100 μm. (c) of FIG. 6 is an image showing liquid droplet spots formed by applying the application liquid 10 of 5% gelatin PBS solution on a slide glass by using an application needle 9 having a tip diameter of 150 μm.

(a), (b), and (c) of FIG. 6 successfully demonstrated that the liquid droplet spots formed had liquid droplet spot diameters approximately proportional to the diameters (50 μm, 100 μm, and 150 μm) of the application needles 9 (the 50-μm application needle: a liquid droplet spot diameter of 75±2 μm; the 100-μm application needle: a liquid droplet spot diameter of 137±3 μm; and the 150-μm application needle: a liquid droplet spot diameter of 219═5 μm).

Experimental Example 3

In application experiment 3, human dermal fibroblasts (NHDF) were dispersed at a concentration of $2\times10^7$ cells/mL in 10% gelatin PBS solution to prepare an application liquid 10. In application experiment 3, the micro-applicator 1 was used to apply the application liquid 10 on a slide glass by contact application using three different application needles 9 with a tip diameter of 100 μm, 150 μm, or 200 μm. The shapes of liquid droplet spots formed on the slide glass by the application were observed under a phase-contrast microscope.

Figure 7:
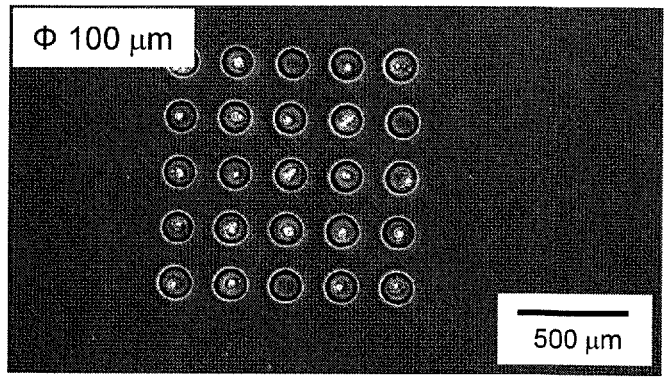
FIG. 7 is photographs showing images of liquid droplet spots observed under a phase-contrast microscope in application experiment 3.
Figure 7:
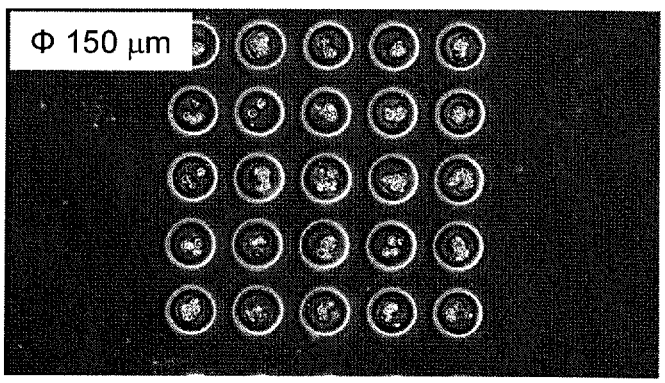
Figure 7:
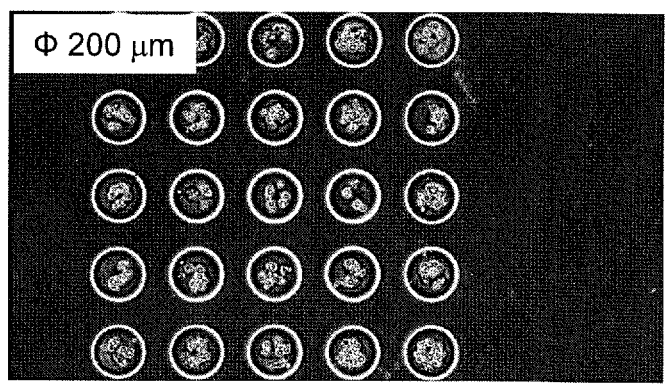

FIG. 7 is photographs showing images of the liquid droplet spots observed under a phase-contrast microscope in application experiment 3. (a) of FIG. 7 is an image showing liquid droplet spots formed by applying the NHDF-dispersed 10% gelatin PBS solution on a slide glass by using an application needle 9 having a tip diameter of 100 μm. (b) of FIG. 7 is an image showing liquid droplet spots formed by applying the NHDF-dispersed 10% gelatin PBS solution on a slide glass by using an application needle 9 having a tip diameter of 150 μm. (c) of FIG. 7 is an image showing liquid droplet spots formed by applying the NHDF-dispersed 10% gelatin PBS solution on a slide glass by using an application needle 9 having a tip diameter of 200 μm.

According to application experiment 3, when the application needle 9 having a tip diameter of 100 μm was used, one liquid droplet spot was found to contain 0 to 3 cells applied. When the application needle 9 having a tip diameter of 150 μm was used, one liquid droplet spot was found to contain 2 to 6 cells applied. In addition, one liquid droplet spot formed using the application needle 9 having a tip diameter of 200 μm was found to contain up to about 10 cells applied. Hence, by selecting the tip diameter of the application needle 9, it was found to be possible to control the number of cells applied in each liquid droplet spot to within about 1 to 10.

Experimental Example 4

In application experiment 4, instead of human dermal fibroblasts (NHDF) in the above application experiment 3, a liver cancer cell line (HepG2) was used to likewise conduct an experiment. In application experiment 4, HepG2 was dispersed at a concentration of $5\times10^7$ cells/mL in 10% gelatin PBS solution to prepare an application liquid 10.

Figure 8:
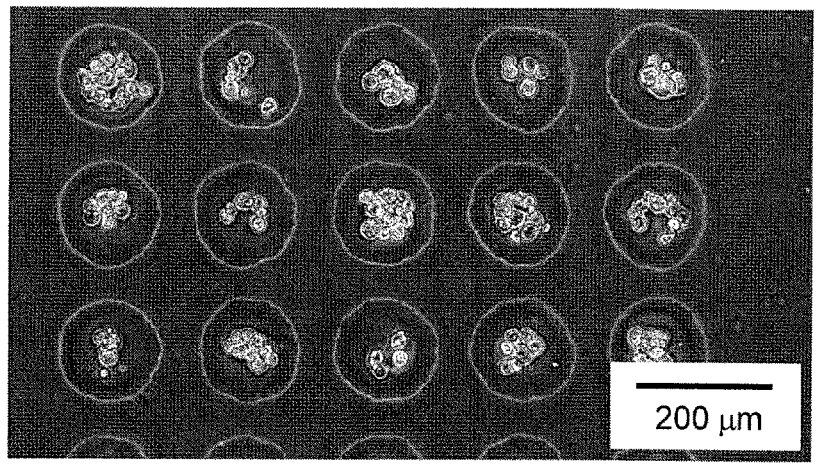
FIG. 8 is photographs showing images of liquid droplet spots observed under a phase-contrast microscope in application experiment 4.

FIG. 8 is an image showing liquid droplet spots formed by applying the HepG2-dispersed 10% gelatin PBS solution on a slide glass by using an application needle 9 having a tip diameter of 100 μm. Even application experiment 4 demonstrated that a given number of cells were present in each liquid droplet spot, so that stable application was possible regardless of the kind of cells. In the below-described application experiment 5, how the tip diameter of the application needle 9 correlated to the number of cells applied and contained in each liquid droplet spot formed was investigated.

Experimental Example 5

In application experiment 5, iPS-derived cardiomyocytes (iPS-CM) were dispersed at a concentration of $4\times10^7$ cells/mL in PBS solution to prepare an application liquid 10 and respective application needles 9 with a tip diameter of 70 µm, 100 µm, 150 µm, 200 µm, or 330 µm were used to form liquid droplet spots. In application experiment 5, how the tip diameter of each application needle 9 correlated to the number of cells applied and contained in each liquid droplet spot formed was investigated.

In application experiment 5, the above application liquid 10 was applied once on a slide glass, and the number of cells after the application was calculated by fluorescence microscopy (using cells, the nuclei of which were stained with a fluorescent dye DAPI) and phase-contrast microscopy. In this application experiment 5, 20 or more liquid droplet spots formed by each of the application needles 9 with a tip diameter of 50 µm, 100 µm, 150 µm, 200 µm, or 330 µm were measured and averaged.

Figure 9:
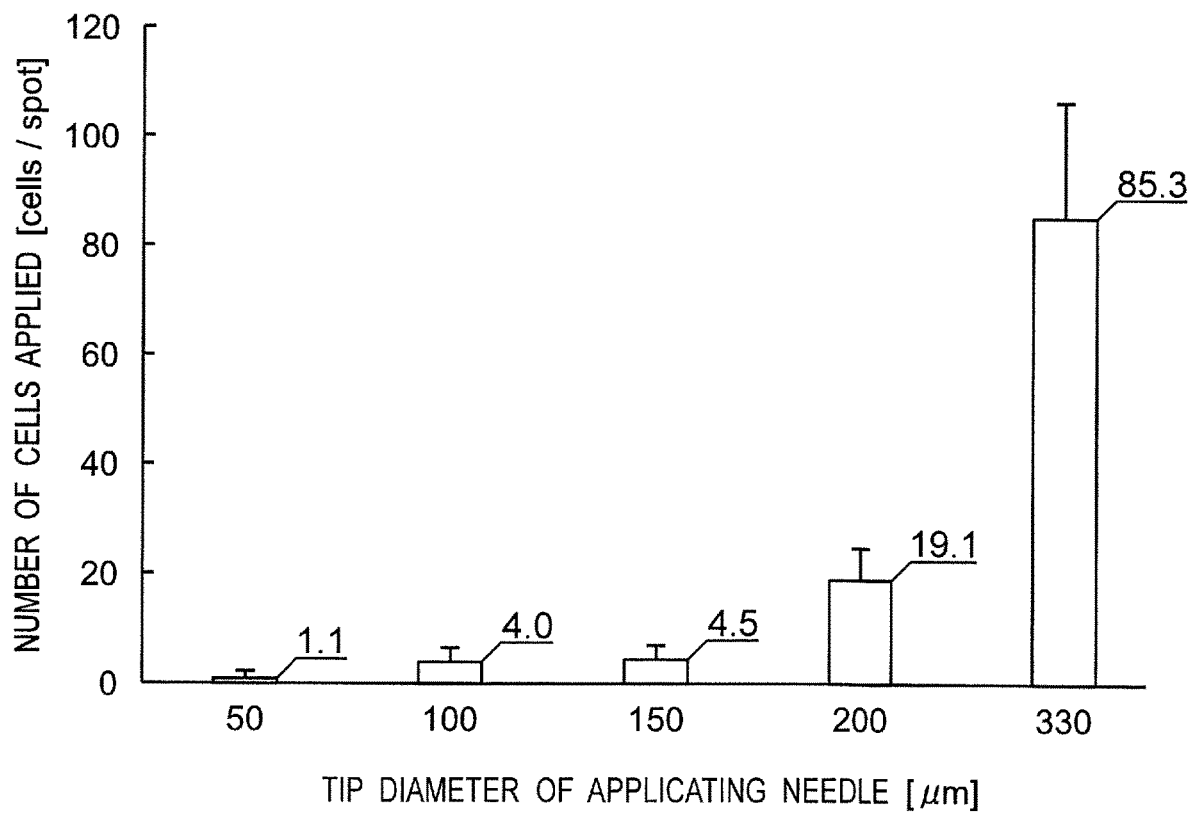
FIG. 9 is a graph showing the experimental results of application experiment 5.

FIG. 9 is a graph showing the experimental results of application experiment 5. In FIG. 9, the ordinate represents the number of cells applied [cells/spot], and the abscissa represents the tip diameter of application needle 9 [µm]. As shown in FIG. 9, when iPS-CM was dispersed at a concentration of $4\times10^7$ cells/mL in PBS solution, average 1.1 cells applied were present in each liquid droplet spot applied by using the application needle 9 with a tip diameter of 50 µm. Average 4.0 cells applied were present in each liquid droplet spot obtained by using the application needle 9 with a tip diameter of 100 µm; average 4.5 cells applied were present in each liquid droplet spot obtained by using the application needle 9 with a tip diameter of 150 µm; average 19.1 cells applied were present in each liquid droplet spot obtained by using the application needle 9 with a tip diameter of 200 µm; and average 85.3 cells applied were present in each liquid droplet spot obtained by using the application needle 9 with a tip diameter of 330 µm. Note that in FIG. 9, the error bars indicate the standard deviations (in the positive direction) of the number of cells applied using the respective application needles 9.

As described above, the tip diameter of each application needle 9 used was correlated with the number of cells applied and present in each liquid droplet spot formed, indicating that as the tip diameter of the application needle 9 became larger, the number of cells applied and present in each liquid droplet spot increased. Hence, by selecting the tip diameter of the application needle 9, it was successfully verified that the number of cells applied in each liquid droplet spot was able to be controlled to within a certain range.

Experimental Example 6

In application experiment 6, the micro-applicator 1 was used to produce a cell assembly 20. In application experiment 6, human dermal fibroblasts (NHDF) were dispersed at a concentration of $2\times10^7$ cells/mL in 2.5% alginic acid PBS solution to prepare an application liquid 10. This application liquid 10 was charged into the application liquid container 8 of the application unit 6, and cell application operation was then executed by the micro-applicator 1.

Figure 10:
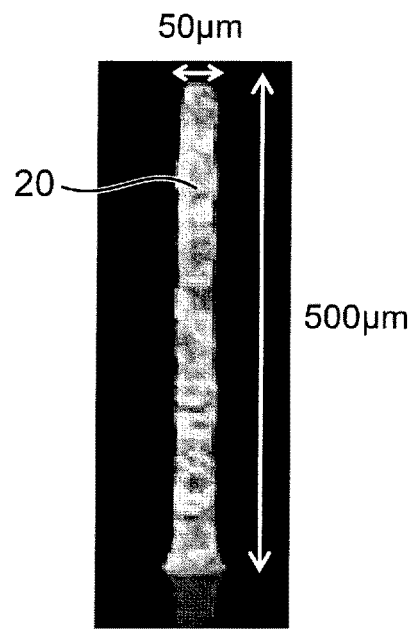
FIG. 10 is an image picture showing a cell assembly produced in application experiment 6.

In application experiment 6, by using an application needle 9 (see (c) of FIG. 3) having a tip 9a with a stepped protrusion 9b and a tip diameter of 100 µm, the alginic acid-containing cell dispersion was consecutively applied 1600 times on a slide glass. At that time, the needle tip was shifted upward by 0.5 µm every cell application operation to produce a cell assembly 20. This resulted in production of the cell assembly 20 with a diameter of 50 µm and a height of 500 µm. FIG. 10 is an image picture showing a cell assembly 20 produced in application experiment 6.

As described above, the cell assembly 20 with a desired shape was found to be able to be produced by repeating multiple cycles of cell application operation while the stop position of the tip 9a of the application needle 9 was shifted upward (e.g., by 0.5 µm), with respect to a certain application target position (certain point) on the substrate 11, per cycle during the application step in the cell application operation.

Experimental Example 7

Figure 11:
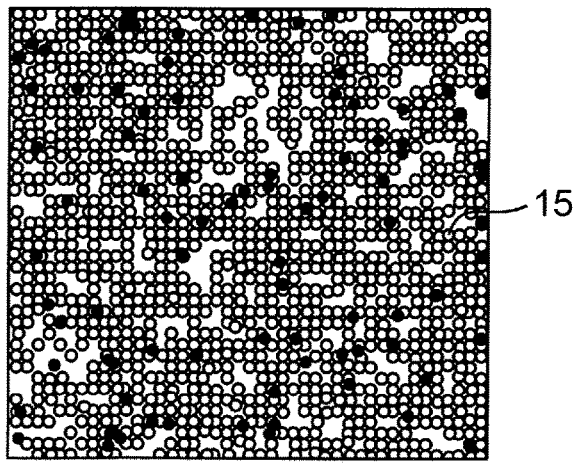
FIG. 11 is pictures showing viable cell/dead cell (Live/Dead) fluorescently stained images in application experiment 7.
Figure 11:
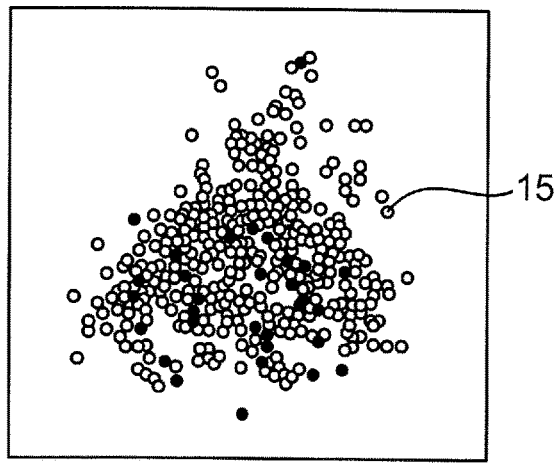

In application experiment 7, the viability of cells applied in liquid droplet spots formed by application using the micro-applicator 1 was examined. In application experiment 7, human dermal fibroblasts (NHDF) were dispersed at a concentration of $8\times10^7$ cells/mL in PBS solution to prepare an application liquid 10. In addition, in application experiment 7, this application liquid 10 was consecutively applied 40 times on a slide glass by using the application needle 9 with a tip diameter of 330 µm, and the viability of cells 15 after the application was evaluated by viable cell/dead cell (Live/Dead) fluorescent staining (dead cells were stained red). FIG. 11 is pictures showing viable cell/dead cell (Live/Dead) fluorescently stained images in application experiment 7.

In FIG. 11, (a) shows a viable cell/dead cell (Live/Dead) fluorescently stained image of cells 15 in a pre-application application liquid 10 and (b) shows a viable cell/dead cell (Live/Dead) fluorescently stained image of cells 15 in a post-application liquid droplet spot. Note that in the viable cell/dead cell (Live/Dead) fluorescently stained images in application experiment 7, viable cells were stained green and dead cells were stained red. Here, in the pictures showing the viable cell/dead cell (Live/Dead) fluorescently stained images in FIG. 11, viable cells were denoted by ○ and dead cells were denoted by ●.

The results of examining the cell 15 viability in application experiment 7 demonstrated that the pre-application cell viability was 96% and the post-application cell viability was 91% and still high. This result clearly confirmed that during the cell application operation using the micro-applicator 1, almost no damage was given directly to the cells 15. Note that the pre-application cell viability was slightly dropped from 96% to the post-application cell viability of 91%. Here, this drop was a regular decrease occurring over time and was caused by another factor.

Experimental Example 8

In application experiment 8, the micro-applicator 1 was used to construct a three-dimensional tissue chip having iPS-derived cardiomyocytes (iPS-CM) on a cell disc. Then, pulsation behavior of a myocardial tissue body on the three-dimensional tissue chip was assessed.

In application experiment 8, iPS-CM was dispersed at a concentration of $4\times10^7$ cells/mL in 20 mg/mL fibrinogen solution to prepare an application liquid 10. In application experiment 8, application was consecutively carried out 10 times on a cell disc by using the application needle 9 with a tip diameter of 330 µm, and the cell disc was then soaked in 800 unit/mL (8.3 mg/mL) thrombin solution to immobilize a tissue by gelatination. Thrombin action caused fibrinogen to form fibrin (blood coagulation-related protein), and this gelatination reaction was utilized to immobilize a tissue on a substrate.

After that, during 6 days of culturing, pulsation behavior was recorded over time under a phase-contrast microscope. As a result, immediately after the application, myocardial tissue bodies with a diameter of about 300 μm were formed and even after 6 days of culturing, the structure of equally spaced myocardial tissue bodies was able to be observed.

Figure 12:
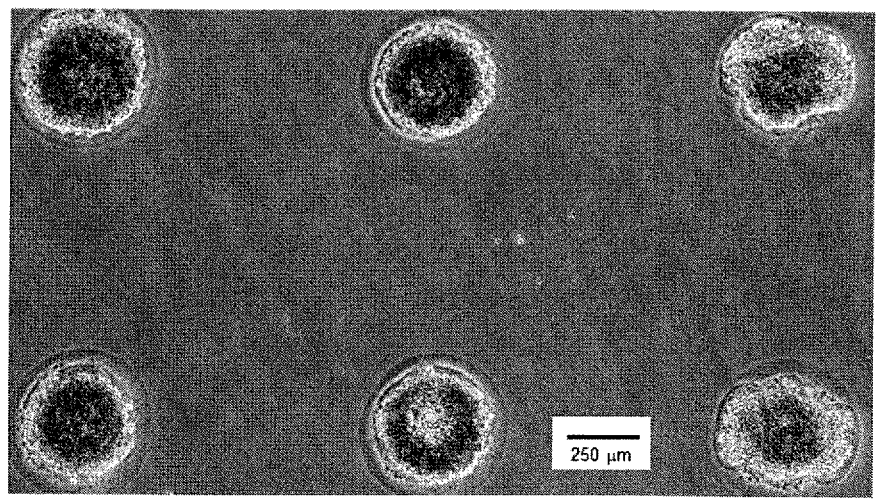
FIG. 12 is a photograph showing images of states of myocardial tissue bodies, produced in application experiment 8, immediately after application.
Figure 13:
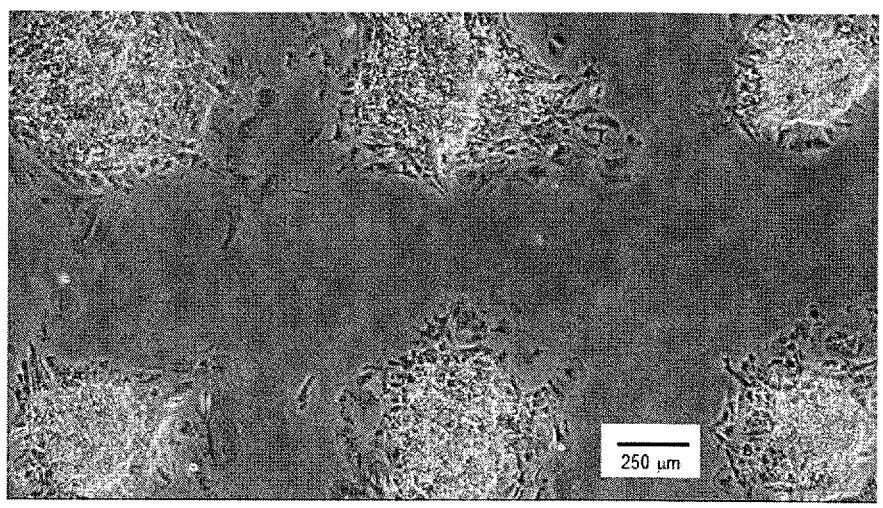
FIG. 13 is a photograph showing images of states of the myocardial tissue bodies shown in FIG. 12 after 6 days of culturing.
Figure 14:
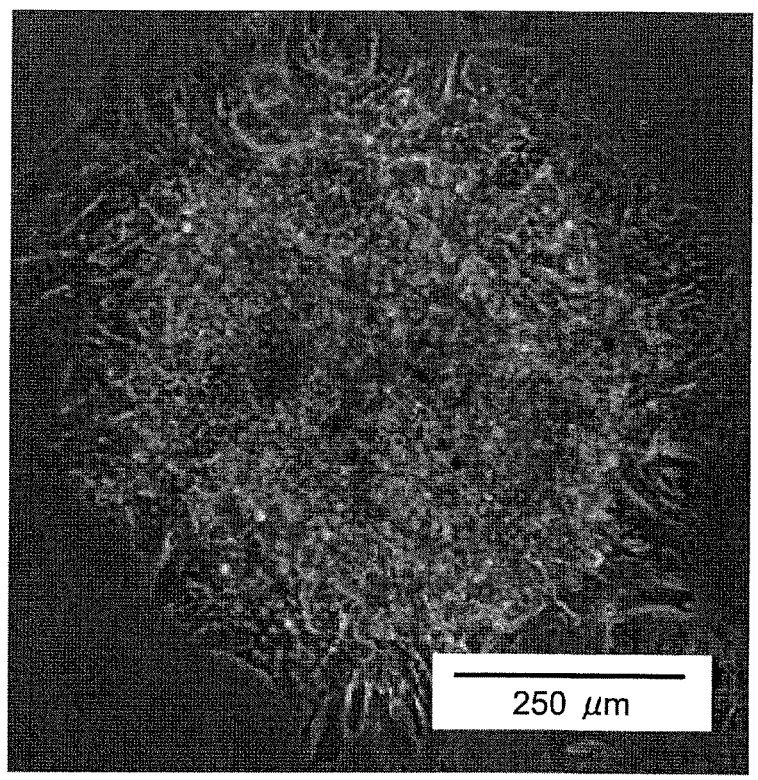
FIG. 14 is a photograph showing an enlarged image of one of the myocardial tissue bodies after 5 days of culturing.

FIG. 12 is a photograph showing states (at culture day 0) of myocardial tissue bodies, produced in application experiment 8, immediately after application. FIG. 13 is a photograph showing states of the myocardial tissue bodies shown in FIG. 12 after 6 days of culturing. FIG. 14 is an enlarged image of one of the myocardial tissue bodies after 5 days of culturing. FIGS. 13 and 14 demonstrated that the structure of each myocardial tissue body was examined and a three-dimensional tissue chip was found to be reliably constructed.

In the myocardial tissue bodies produced, cardiomyocytes started pulsation after culture day 2, and at culture day 6, average 82 pulsations per min were recorded in 6 samples. The standard deviation of the 6 samples was 15.

Figure 15:
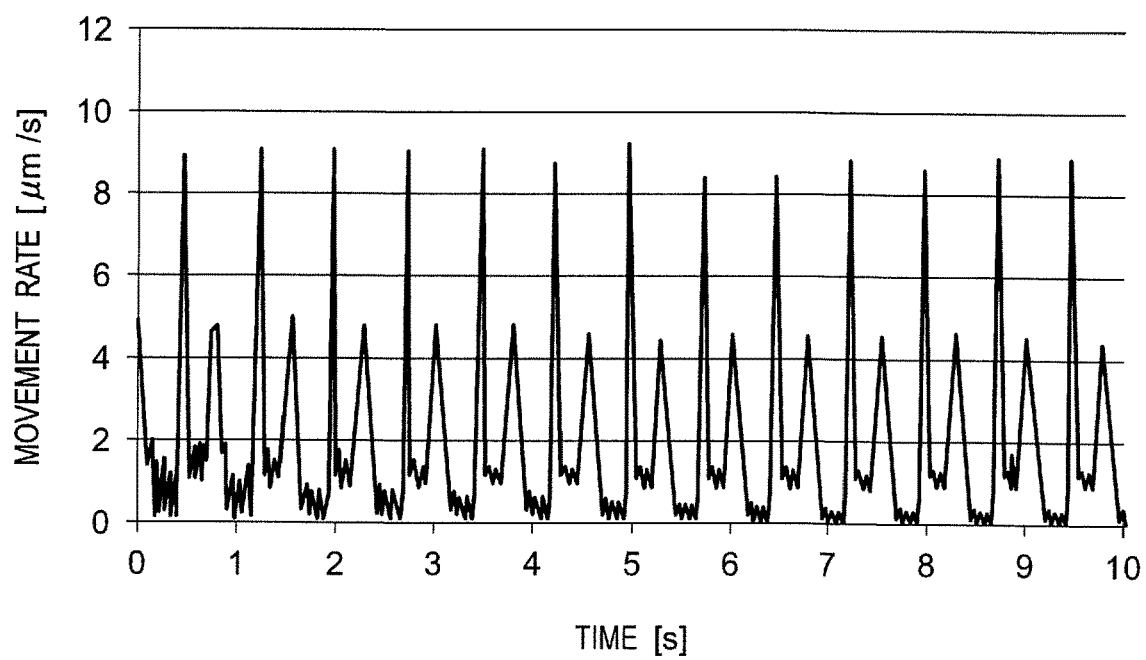
FIG. 15 is a graph showing a contraction-relaxation rate obtained by analyzing a pulsation video of the myocardial tissue body cultured for 5 days as shown in FIG. 14.

In addition, a pulsation video captured using a high-speed camera was analyzed to calculate a contraction-relaxation rate with a constant cycle. FIG. 15 is a graph showing a contraction-relaxation rate obtained by analyzing a pulsation video of the myocardial tissue body (three-dimensional tissue chip) cultured for 5 days as shown in FIG. 14. In FIG. 15, the ordinate represents a movement rate at which the myocardial tissue body contracts and relaxes, and the abscissa represents time [s].

As shown in FIG. 15, the myocardial tissue body (three-dimensional tissue chip) exhibited constant pulsations and the contraction-relaxation rate with a constant cycle was found. At that time, the pulsation rate was 78 times/min, the average contraction rate was 8.7 μm/s, and the average relaxation rate was 4.6 μm/s.

The myocardial tissue bodies obtained in the above application experiment 8 may be produced in respective wells on, for instance, a 96-well plate. This makes it possible to produce a high-throughput cardio-toxicity evaluation kit allowing for automated robotic evaluation under aseptic conditions.

Second Embodiment

Next, a method for producing a cell chip or three-dimensional tissue chip according to a second embodiment of the invention will be described with reference to the Drawings attached. An apparatus having the same configuration and functions as of the micro-applicator 1 used in the above-described first embodiment is used as a micro-applicator in the second embodiment. The method for producing a cell chip or three-dimensional tissue chip according to the second embodiment is as described in, for instance, paragraph [0044] regarding the cell application operation in the above first embodiment. Here, an example of the cell chip or three-dimensional tissue chip production method is described in which the needle tip is shifted upward by a given distance every cycle of cell application operation. That is, in the method for producing a cell chip or three-dimensional tissue chip according to the second embodiment, a specific example of the cell chip or three-dimensional tissue chip production method described in the first embodiment is explained. Note that, in the description for the second embodiment, elements having the same action, structure, and function as of the above first embodiment may have the same reference numerals so as to omit and avoid redundant description.

Figure 16:
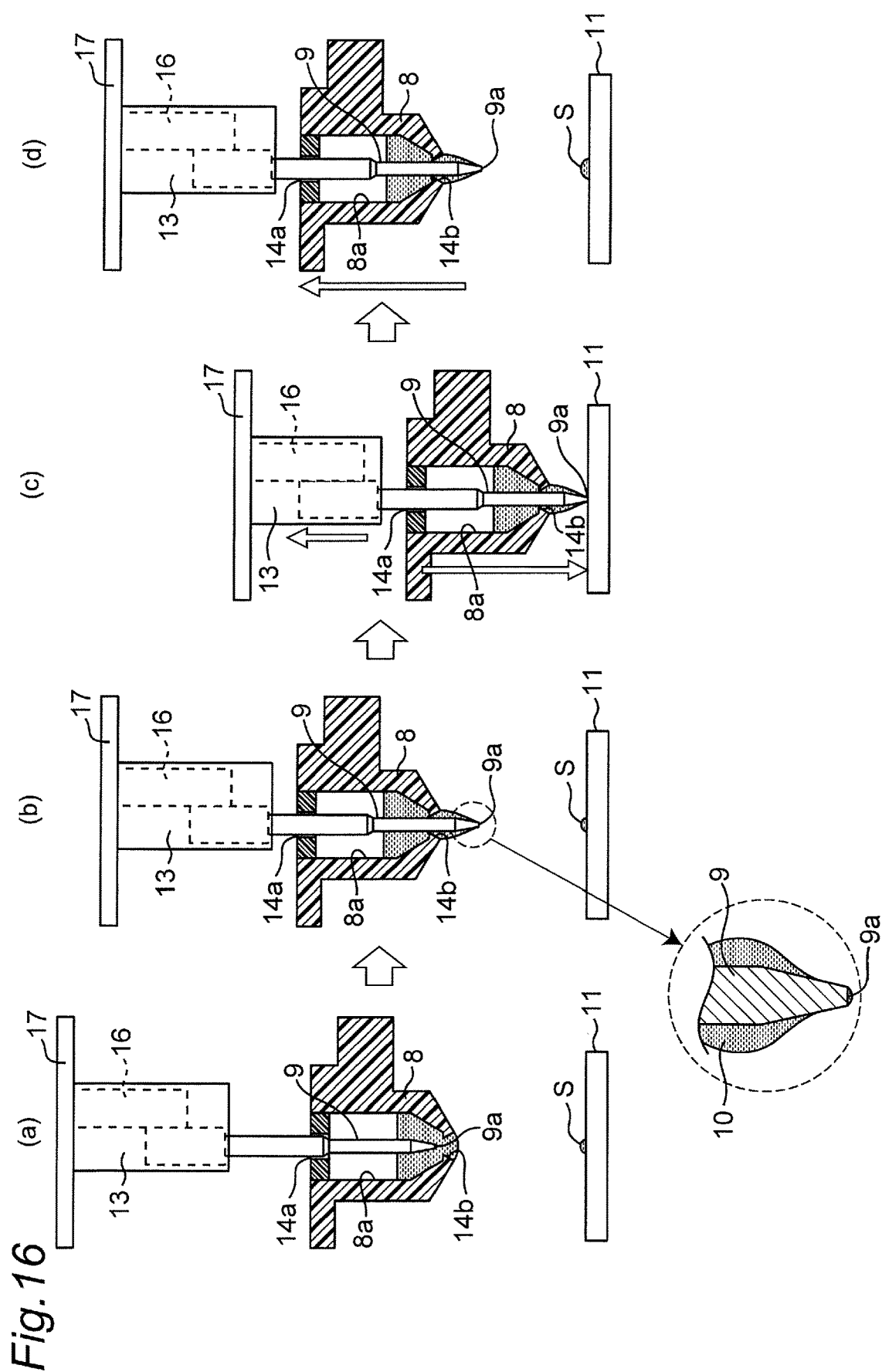
FIG. 16 is diagrams schematically illustrating cell application operation in a method for producing a cell chip or three-dimensional tissue chip according to a second embodiment of the invention.

FIG. 16 is diagrams schematically illustrating cell application operation in the method for producing a cell chip or three-dimensional tissue chip according to the second embodiment. The cell application operation shown in FIG. 16 represents one cycle of cell application operation. In the cell application operation shown in FIG. 16, the tip 9a of the application needle 9 is subjected to contact application on the substrate 11, which is an application target, and a state is illustrated in which a liquid droplet spot S (cell assembly 20) of the application liquid 10, which is a cell-containing solution, has already been formed on the substrate 11. That is, the cell application operation in FIG. 16 represents a cell application operation in at least the second cycle or later after the first cycle of cell application operation has been executed.

(a) of FIG. 16 shows an attachment state (attachment step) in which the tip 9a of the application needle 9 is dipped into the application liquid 10 in the application liquid reservoir 8a and the application liquid 10 is attached to the tip 9a of the application needle 9, and this state corresponds to a waiting state during the cell application operation in the first embodiment.

(b) of FIG. 16 shows a transfer state (transfer step) in which the tip 9a of the application needle 9 is projected from the lower hole 14b at the application liquid container 8 and the tip 9a descends toward the substrate 11 from the application liquid reservoir 8a. That is, (b) of FIG. 16 corresponds to a descending state during the cell application operation in the first embodiment.

(c) of FIG. 16 shows a contact application state (application step) in which the tip 9a of the application needle 9 comes into contact with a liquid droplet spot S on the substrate 11. The liquid droplet spot S of the application liquid 10 applied at that time corresponds to a certain volume of application liquid 10 attached to the tip 9a of the application needle 9.

(d) of FIG. 16 shows a state after the application needle 9 is used to apply the application liquid 10 on a surface of the substrate 11 and shows a separation state (separation step) in which the application needle 9 has been separated and is being lifted from the substrate 11. That is, (d) of FIG. 16 corresponds to a holding state during the cell application operation in the first embodiment.

As described above, in the second embodiment, the one cycle of cell application operation includes, in sequence, (a), (b), (c), (d), and (a) operations as illustrated in FIG. 16. In the second embodiment, the one cycle of cell application operation is conducted in 0.1 sec, and the cell application operation is executed in a ultra-short period. Regarding the cell application operation in the second embodiment, the tip 9a of the application needle 9 is controlled such that the stop position at the time of contact application is gradually shifted upward after the cell application operation at the second cycle or later.

Figure 17:
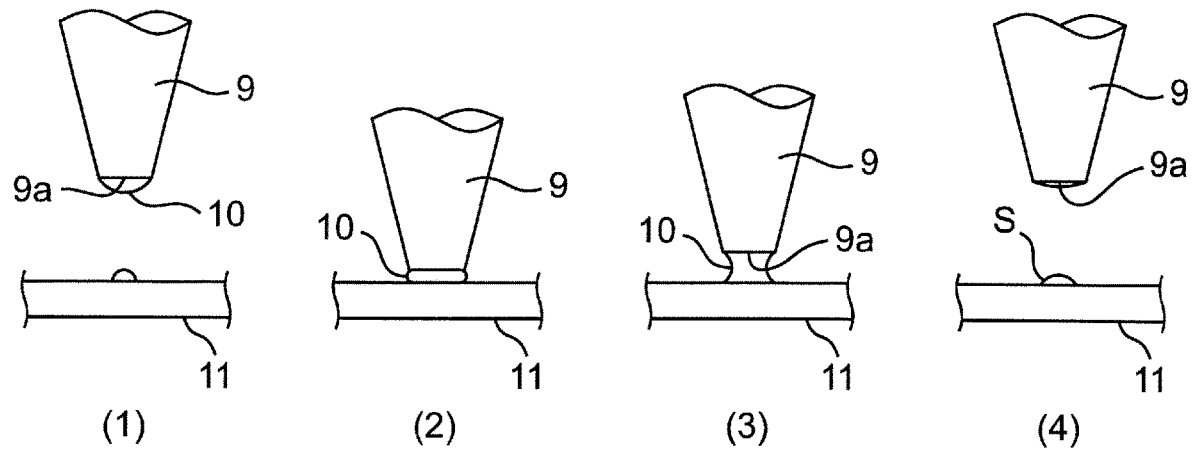
FIG. 17 is diagrams schematically illustrating movements of an application needle during cell application operation in the method for producing a cell chip or three-dimensional tissue chip according to the second embodiment.

Diagrams (1) to (4) shown in FIG. 17 are diagrams schematically illustrating movements of the tip 9a of the application needle 9 during contact application in the cell application operation. FIG. 17 schematically illustrates: (1) a state in which the application liquid 10, which is a tiny volume of cell-containing solution, has been attached to the tip 9a of the application needle 9; (2) a state in which the application liquid 10 attached to the tip 9a of the application needle 9 comes into contact with a liquid droplet spot S of the application liquid 10 that is an application target and has already been applied onto the substrate 11; (3) a state immediately after the tip 9a of the application needle 9 has come into contact with the application liquid 10 on the substrate 11 and is then lifted; and (4) a state in which the tip 9a of the application needle 9 is lifted and separated from the substrate 11 and a new liquid droplet spot S is formed on the substrate 11.

As described above, in the cell application operation at the second cycle or later according to the second embodiment, the tip 9a of the application needle 9 does not come into contact with the substrate 11, but comes into contact with the application liquid 10 on the substrate 11 and is thus subject to contact application to produce a desired cell chip or three-dimensional tissue chip.

Figure 18:
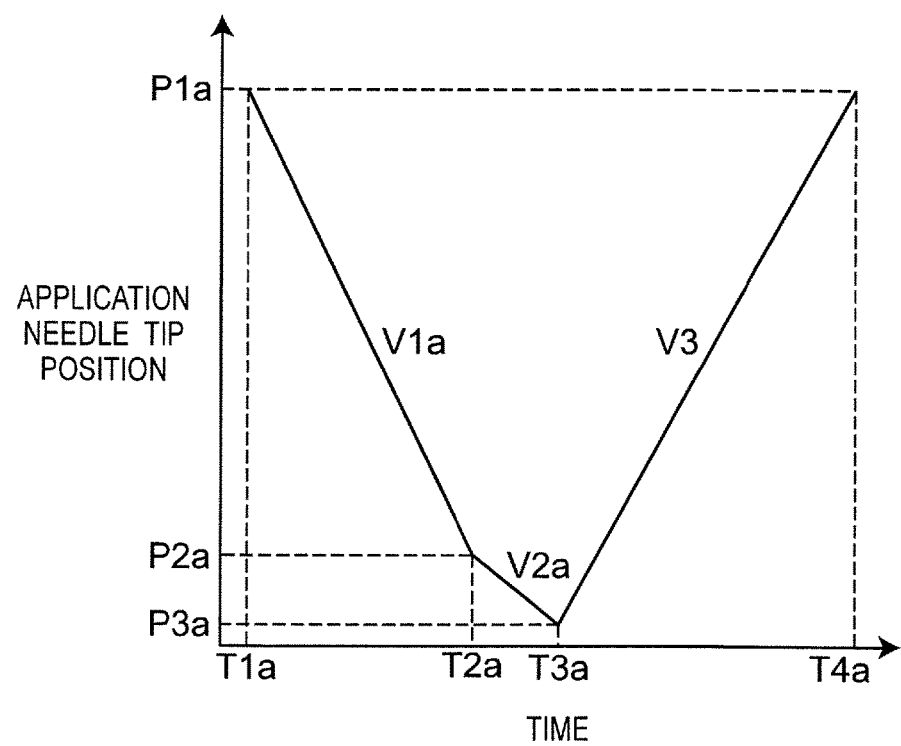
FIG. 18 is an operation graph describing movements of an application needle during cell application operation in the method for producing a cell chip or three-dimensional tissue chip according to the second embodiment.

FIG. 18 is an operation graph describing movements of the tip 9a of the application needle 9 during the cell application operation. In the operation graph of FIG. 18, the ordinate represents an application needle tip position, and the abscissa represents time.

As shown in FIG. 18, during the cell application operation of the application needle 9, its tip 9a descends at a first application velocity V1a from an upper limit position P1a and descends at a low speed of second application velocity V2a slower that the first application velocity V1a after having reached a predetermined velocity change position P2a immediately before the application. The tip 9a of the application needle 9 descends at the second application velocity V2a, and the application liquid 10 attached to the tip 9a is subjected to contact application at a contact application position P3a. The contact application position P3a may be pre-set by calculating the position and height over the application target substrate 11 on the basis of data detected with, for instance, a position meter installed at a measuring device. Note that the micro-applicator 1 is provided with: a horizontally movable XY table 4; a finely adjustable application unit 6 that moves in the top-to-bottom direction (vertical direction) relative to the XY table 4; an observation optical unit (e.g., a CCD camera) such as an optical detection unit 7 configured to, for instance, visually examine an applied material (e.g., cells) over the XY table 4; and a measuring device (e.g., a laser displacement meter, a white light interference meter) including a measuring instrument configured to, for instance, measure an applied material produced.

Regarding the contact application position P3a, an original starting position of application at the first cycle of the cell application operation may be detected and then pre-set. Based on the starting position, a contact application position P3a at the second time or later in the application operation may be set. That is, during a plurality of cycles of the cell application operation using the application needle 9, the contact application position P3a may be gradually shifted upward every cell application operation as long as the contact application is permitted.

During the cell application operation, the contact application at the contact application position P3a is followed by return to the upper limit position P1a, which is the initial operation position, at a return velocity V3. Then, the next cell application operation is repeated. As shown in FIG. 18, during one cycle of the cell application operation, the needle descends at the first application velocity V1a from the upper limit position P1a (at time T1a) to the velocity change position P2a (at time T2a), descends at the second application velocity V2a (<V1a) from the velocity change position P2a (at time T2a) to the contact application position P3a (at time T3a), and is then subjected to contact application. After the contact application, the needle ascends toward the upper limit position P1a (at time T4a) at a prescribed return velocity V3.

Regarding the micro-applicator 1 in the second embodiment, the second application velocity V2a of the application needle 9 when reaching the contact application position P3a is lower than the first application velocity V1a. This enables the tip 9a of the application needle 9 to be positioned, with high precision, on the pre-set contact application position P3a, thereby capable of executing finely tuned cell application operation. Note that even if the tip 9a of the application needle 9 is brought into contact with the application target substrate surface, the resulting contact impact can be small and the cells may thus be affected little.

Figure 19:
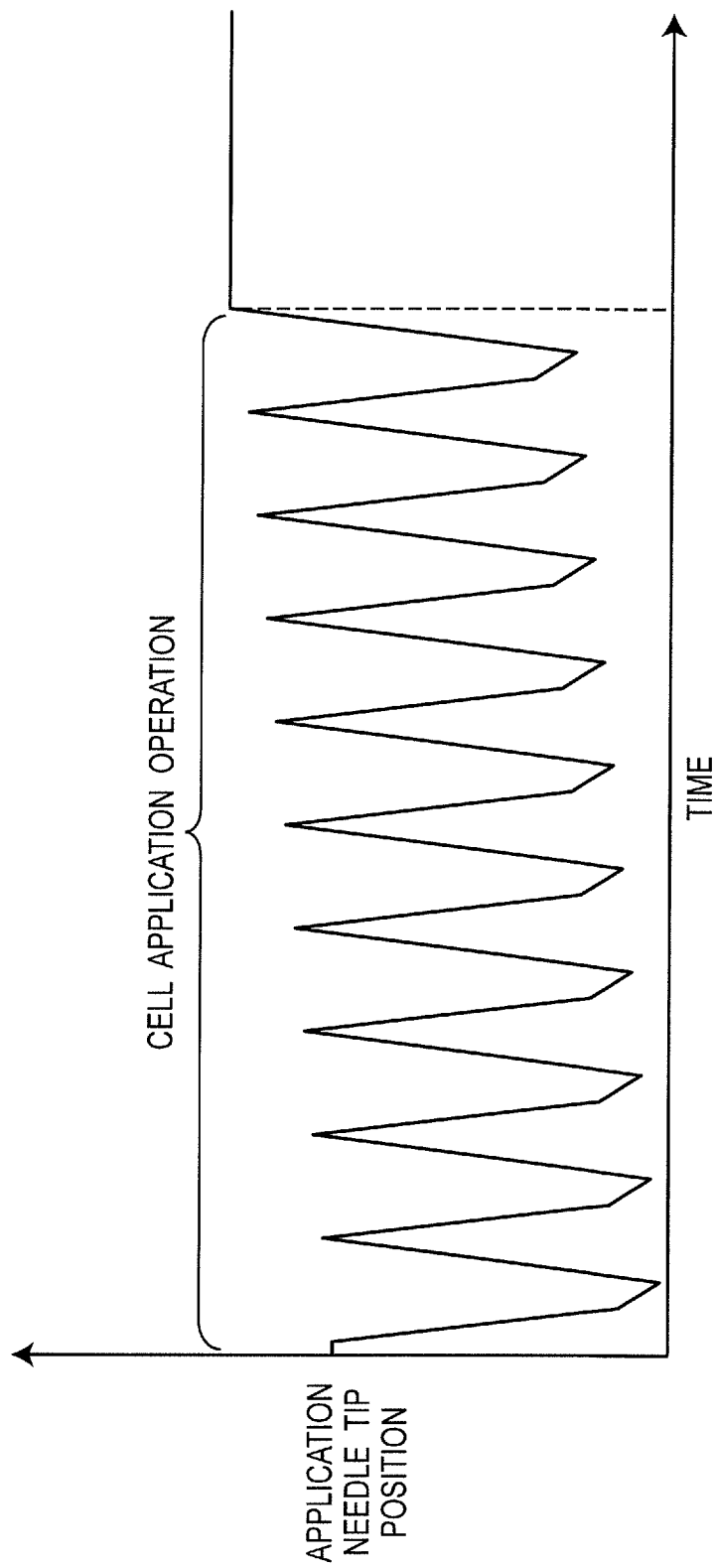
FIG. 19 is an operation chart describing multiple cycles of cell application operation for a micro-applicator in the second embodiment.

FIG. 19 is an operation chart describing multiple cycles of cell application operation for the micro-applicator 1 in the second embodiment. In the cell application operation shown in FIG. 19, the cell contact application, in which the application liquid 10 is applied on the application target substrate 11 by using the application needle 9, is repeated 10 times.

As illustrated in FIG. 19, during 10 times of contact application in the cell application operation, the contact application position P3a, which is the lowest position of the application needle 9, is set and gradually shifted upward every time a single contact application is completed. Regarding the cell application operation in the micro-applicator 1 in the second embodiment, the contact application position P3a is shifted upward by several μm every cycle.

Figure 20:
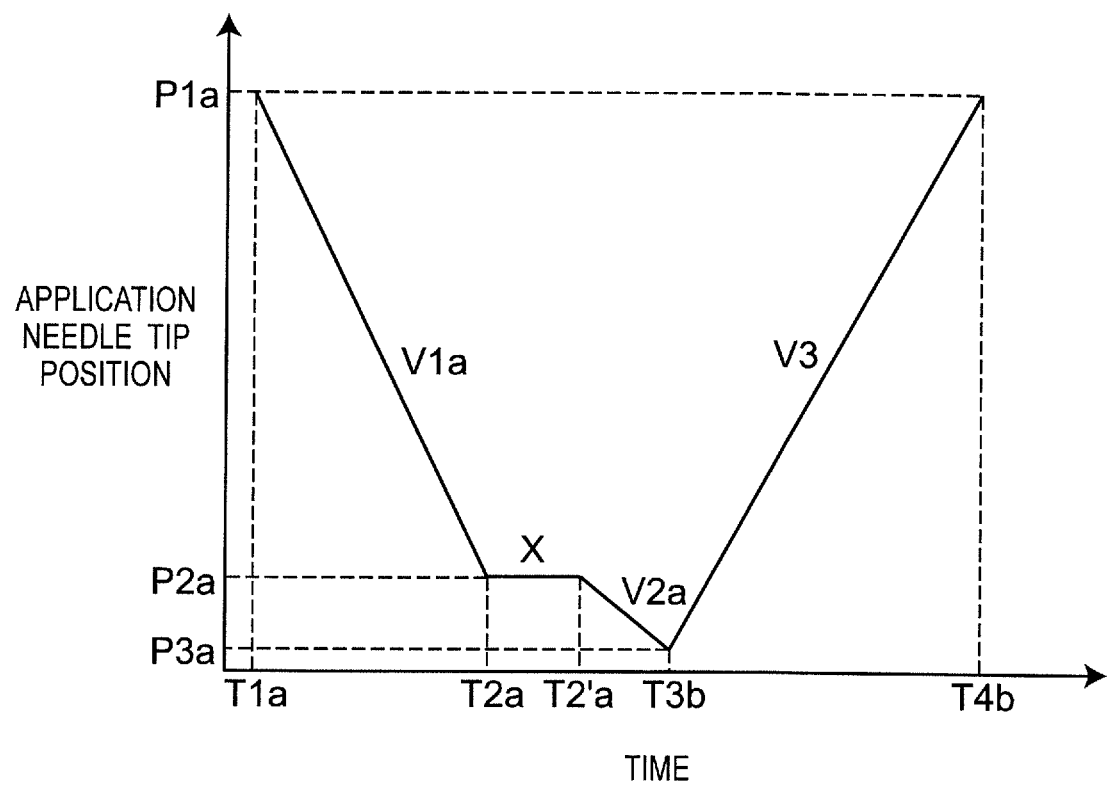
FIG. 20 is an operation graph showing a modification embodiment regarding movements of an application needle during cell application operation in the method for producing a cell chip or three-dimensional tissue chip according to the second embodiment.

For the micro-applicator 1 in the second embodiment, movements illustrated in FIG. 20, as a modification embodiment of the movements shown in FIG. 18, may be adopted as movements of the tip 9a of the application needle 9 during the cell application operation.

FIG. 20 is an operation graph illustrating cell application operation of the tip 9a of the application needle 9 while the application needle 9 is once paused for a predetermined period at the velocity change position P2a just above the application target. As shown in FIG. 20, the tip 9a of the application needle 9 descends at the first application velocity V1a and reaches the velocity change position P2a. At that time (T2a), the tip stops for a predetermined short period (T2a→T2'a). After this predetermined period has passed, the tip descends again toward the application target at the second application velocity V2a and is then subjected to contact application. As such, the tip 9a of the application needle 9 is stopped only for a predetermined short period at the position just above the application target, so that the volume of the application liquid 10 applied by the tip 9a can be made equal. This makes it possible to stably apply, depending on characteristics of the application liquid, a constant application volume on the application target while the application needle 9 in the micro-applicator 1 is used to perform the cell application operation show in FIG. 20.

As described above, during the cell application operation shown in FIG. 20, the needle is once paused at the velocity change position P2a and descends, at the second application velocity V2a slower than the first application velocity V1a before the pause, toward the contact application position P3a after the predetermined period (X) has passed. The contact application at the contact application position P3a is followed by return to the upper limit position P1a, which is the initial operation position, at the return velocity V3. Then, the next cycle of cell application operation is repeated. As shown in FIG. 20, during one cycle of the application operation, the needle descends at the first application velocity V1a from the upper limit position P1a (at time T1a) to the velocity change position P2a (at time T2a), descends at the second application velocity V2a (<V1a) from the velocity change position P2a (at time T2'a) to the contact application position P3a (at time T3b) after the predetermined period (X) has passed, and is then subjected to contact application. After the contact application, the needle ascends toward the upper limit position P1a (at time T4b) at the prescribed return velocity V3.

Figure 21:
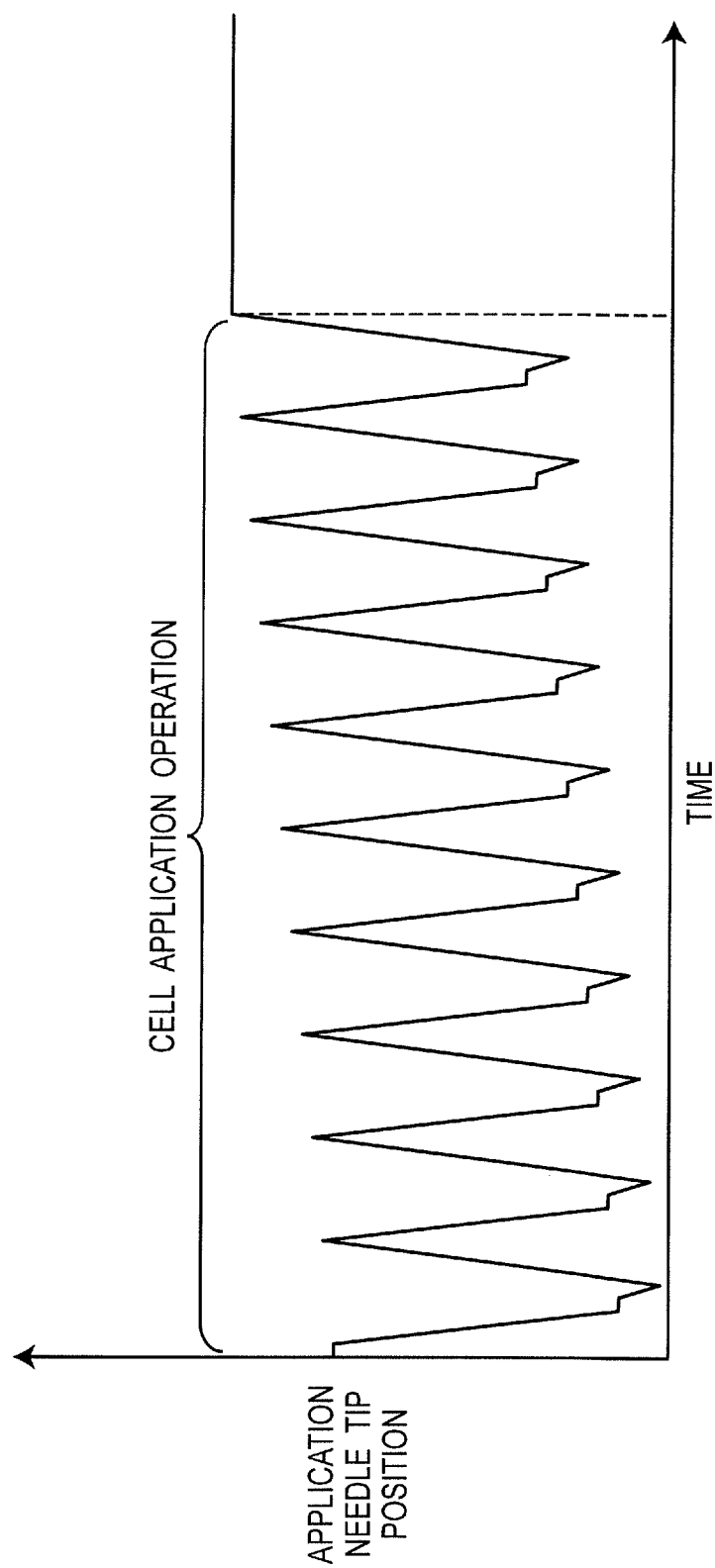
FIG. 21 is an operation chart showing a modification embodiment of multiple cycles of cell application operation in a micro-applicator in the second embodiment.

FIG. 21 is an operation chart illustrating multiple cycles of cell application operation using the application needle 9 as shown in FIG. 20. During the cell application operation using the application needle 9 as illustrated in FIG. 21, the contact application, in which the application needle 9 is used to apply the application liquid 10 on the application target substrate 11, is repeated 10 times.

During the cell application operation illustrated in FIG. 21, like the cell application operation illustrated in FIG. 19, the contact application position P3a, which is the lowest position of the application needle 9, is set and gradually shifted upward every time a single application is completed.

[How to Determine Initial Set Position of Contact Application Position P3]

The following describes how to determine the initial set position, which is the contact application position P3a of the tip 9a of the application needle 9 at the first cycle, during the cell application operation using the micro-applicator 1 in the second embodiment. During the cell application operation, the contact application position P3a of the tip 9a of the application needle 9 is gradually shifted upward every cycle. Before the cell application operation is executed, the initial set position, which is the contact application position P3a at the first cycle during the cell application operation, is determined. Once the initial set position is determined, the contact application position P3a is set and shifted upward, based on the determined initial set position, by a pre-set given distance (e.g., several μm) every cycle.

Figure 22:
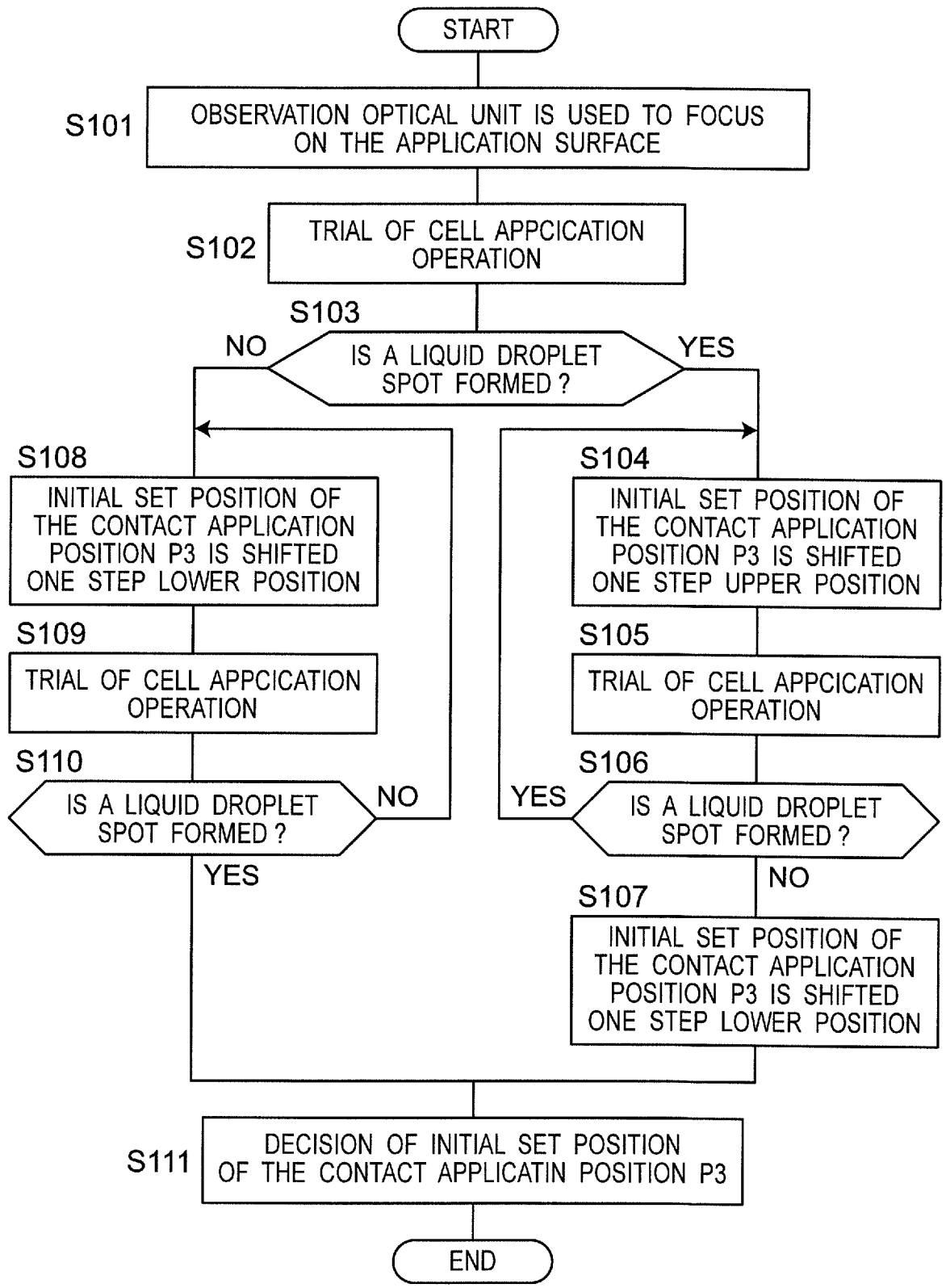
FIG. 22 is a flowchart illustrating how to determine an initial set position with respect to a contact application position in a micro-applicator in the second embodiment.

FIG. 22 is a flowchart illustrating how to determine the initial set position with respect to the contact application position P3a in the micro-applicator 1 in the second embodiment. At step S101, an observation optical unit (e.g., a CCD camera) such as an optical detection unit 7 installed at the micro-applicator 1 is used to focus on an application point, which is on an application surface of an application target (e.g., the substrate 11).

At step 102, the micro-applicator 1 tries to carry out the cell application operation on the application point of the application target. In this trial, the application operation may be executed like actual cell application operation while a reference position based on the focused application point is set as a temporal contact application position P3a. Note that the temporal contact application position P3a, which is initially set in the trial, may be visually determined using the observation optical unit or may be determined based on the position focused using the observation optical unit as described above.

At step 103, the observation optical unit is used to check whether or not a liquid droplet spot S has been formed on the application point of the application target. If formation of a liquid droplet spot S on the application point of the application target is detected, the initial set position is shifted upward to a pre-set, one-step upper position (a several-μm upper position) (step 104). At step 105, the cell application operation is re-tried after the liquid droplet spot S on the application point of the application target has been removed.

At step 106, the observation optical unit is used to check whether or not a liquid droplet spot S is newly formed on the application point of the application target. If a liquid droplet spot S is newly formed on the application point, the process returns to step 104 and the initial set position is shifted upward to an additional one-step upper position. Then, the cell application operation is retried.

At step 106, if any liquid droplet spot S is not formed on the application point, the process goes to step 107. At step 107, the initial set position is shifted downward to a pre-set one-step lower position. This lowered position is determined as and set to the initial set position, which is the contact application position P3a at the first cycle during the cell application operation (step 111).

Meanwhile, if formation of any liquid droplet spot S on the application point of the application target is not detected by the observation optical unit at step 103, the initial set position, which is the contact application position P3a at the first cycle during the cell application operation, is shifted downward to a pre-set, one-step lower position (e.g., a several-μm lower position) (step 108). At step 109, the cell application operation is retried on the application point of the application target.

At step 110, if formation of any liquid droplet spot S on the application point of the application target is not detected by the observation optical unit, the process returns to step 108 and the initial set position is shifted downward to an additional one-step lower position. Then, the cell application operation is retried.

When formation of a liquid droplet spot on the application point is detected at step 110, this position is determined as and set to the initial set position, which is the contact application position P3a at the first cycle during the cell application operation (step 111).

Note that each step in the flowchart shown in FIG. 22 is carried out by executing control programs stored in a memory such as ROM of the display/control unit 3 included in the micro-applicator 1.

By determining the contact application position P3a at the first cycle during the cell application operation as described above, the contact application positions P3a at the respective cycles during the cell application operation are determined. The contact application position P3a at each cycle is set by adding a pre-set prescribed distance (e.g. several μm) to the determined initial set position. The prescribed distance added at that time is set to a distance that secures the contact application.

As described above, the micro-applicator 1 in the second embodiment is set such that in the multiple cycles (e.g., 10 cycles) of contact application during the cell application operation, the contact application position P3a, which is the lowest position, of the tip 9a of the application needle 9 is gradually shifted upward every time a single contact application is completed. For instance, the contact application position P3a is shifted upward by several μm every contact application.

In the method for producing a cell chip or three-dimensional tissue chip by cell application operation using the micro-applicator 1 according to the second embodiment, the contact application is repeated multiple times on the application target or the application liquid 10 on the application target while a tiny volume of application liquid 10 is attached to the tip 9a of the application needle 9. Liquid droplet spots S in an application volume of several pL (picoliter) can be applied and formed with high positional precision, such as positional precision of ±15 μm or less and preferably ±3 μm or less. In addition, in the method for producing a cell chip or three-dimensional tissue chip according to the second embodiment, it is possible to apply a material with a viscosity of the application liquid 10 of $1 \times 10^5$ mPa·s or lower and preferably from 1 to $1 \times 10^4$ mPa·s.

This allows for application of highly viscous cell dispersion. During the cell application operation using the micro-applicator 1 in the second embodiment, a tiny volume of application liquid 10 attached to the tip 9a of the application needle 9 is subjected to contact application, with high precision, on the application target or the application liquid on the application target. This makes it possible to stably and repeatedly apply the application liquid 10. As such, according to the cell application operation using the micro-applicator 1 in the second embodiment, a highly viscous cell dispersion can be precisely applied at a predetermined position relative to the application target. This makes it possible to produce a cell chip with a given pattern or a three-dimensional tissue chip on which cells are shaped three-dimensionally. In view of the above, the method for producing a cell chip or three-dimensional tissue chip according to second embodiment of the invention exerts advantageous effects on progress in respective fields while the produced cell chip or three-dimensional tissue chip is utilized in the fields of regenerative medicine and drug discovery research such as drug efficacy or safety evaluation screening.

Third Embodiment

In the micro-applicator 1 in the first or second embodiment, it is configured such that the application needle 9 is made to penetrate through the application liquid reservoir 8a of the application liquid container 8 and is subjected to contact application on the application target or the application liquid 10 on the application target. The present invention is not limited to such a configuration. For instance, it may be configured such that the application needle dipped in the application liquid of the application liquid reservoir is lifted, moved to an application position, and subjected to contact application. The micro-applicator as so configured can exert substantially the same effects as of the micro-applicator 1 in the above first or second embodiment. Even when a highly viscous cell-containing gelatinizer is a material, a cell chip or three-dimensional tissue chip formed using a desired application volume can be reliably produced within a short time (at a high speed).

Figure 23:
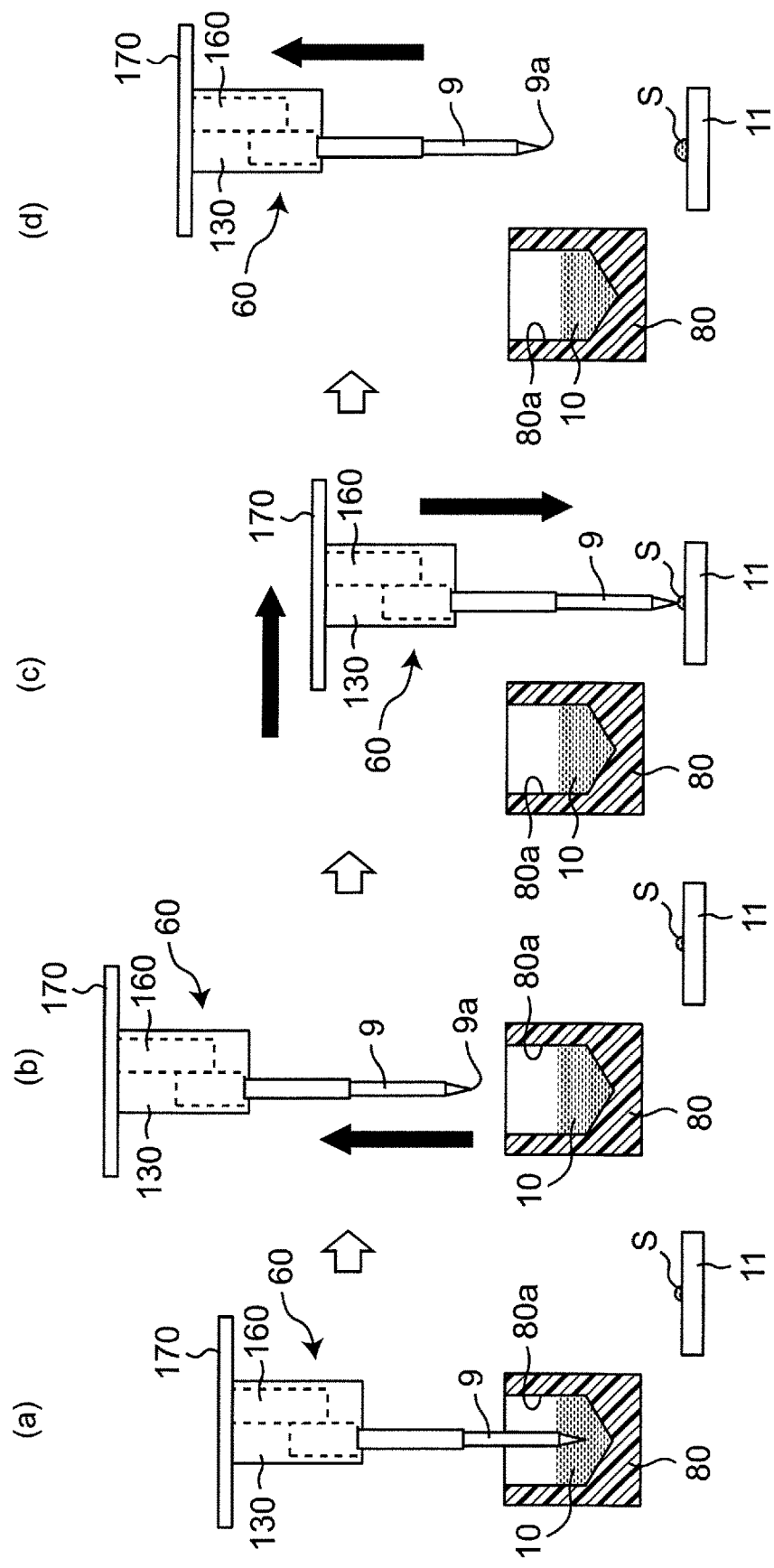
FIG. 23 is diagrams schematically illustrating cell application operation of an application unit in a micro-applicator in a third embodiment according to the invention.

FIG. 23 is diagrams schematically illustrating cell application operation of an application unit 60 in a micro-applicator in a third embodiment. As shown in FIG. 23, the application unit 60 includes: an application liquid container 80 having an application liquid reservoir 80a in which a prescribed amount of application liquid 10, a cell-containing solution, is stored; and an application needle holder part 130 holding the application needle 9 having the tip 9a attached to the application liquid 10 while the application needle 9 is dipped into the application liquid 10 in the application liquid reservoir 80a. The application needle holder part 130 is provided with a sliding mechanism part 160 that slidably holds the application needle 9 in the top-to-bottom direction (vertical direction). The application needle holder part 130 is detachably provided at a given position on a driving mechanism part 170, and, for instance, is detachable from the driving mechanism part 170 by using magnetic force of a magnet. The driving mechanism part 170 is configured such that the application needle 9 held by the mounted application needle holder part 130 is moved to an application position on an application target (e.g., the substrate 11) and is then subjected to contact application.

[Cell Application Operation]

The cell application operation in the application unit 60, as schematically shown in FIG. 23, will be described. During the cell application operation as shown in (a) and (b) of FIG. 23, the tip 9a of the application needle 9 is dipped into the application liquid 10, a cell-containing solution, and the application liquid 10 is attached to the tip 9a of the application needle 9. The tip 9a having the application liquid 10 attached is moved and then comes into contact with an application target, namely the substrate 11 or the application liquid 10 on the substrate 11 to form a liquid droplet spot S on the substrate 11 (see (c) and (d) of FIG. 23). This cell application operation is repeated a predetermined number of times and the application liquid 10 is subjected to multiple cycles of contact application to produce a desired cell chip or three-dimensional tissue chip on the substrate 11.

(a) of FIG. 23 shows an attachment step during the cell application operation. In this attachment step, the tip 9a of the application needle 9 is dipped into (held in) the application liquid 10, which is a cell-containing solution stored in the application liquid reservoir 80a of the application liquid container 80.

(b) of FIG. 23 shows a transfer step in which the tip 9a of the application needle 9 is lifted and the tip 9a moves toward the substrate 11 from the application liquid reservoir 80a. During this transfer step, the application liquid 10 is attached to the tip 9a of the application needle 9 and the surface tension of the application liquid 10 attached causes the tip 9a of the application needle 9 to securely retain a certain volume of application liquid 10. Note that the final stage of this transfer step includes at least an operation in which the application needle descends toward the application target.

(c) of FIG. 23 shows an application step of bringing the tip 9a of the application needle 9 into contact with the application target, namely the substrate 11 or the application liquid 10 on the substrate 11 to form a liquid droplet spot S on the substrate 11. The liquid droplet spot S of the application liquid 10 contact-applied at that time corresponds to the volume of application liquid 10 attached to the tip 9a of the application needle 9.

(d) of FIG. 23 shows a state immediately after the application needle 9 is used to apply the application liquid 10 on a surface of the substrate 11 and shows a separation step in which the application needle 9 is lifted from the substrate 11 and moves toward the application liquid reservoir 80a of the application liquid container 80. That is, the separation step is in a state in which after the application liquid 10, a cell-containing solution, is subjected to contact application, the tip 9a of the application needle 9 is separated from the application target. This separation step is followed by transition to the attachment step in which the tip 9a of the application needle 9 is dipped into (held in) the application liquid 10 of the application liquid reservoir 8a.

As described above, the one cycle of cell application operation includes, in sequence, (a), (b), (c), (d), and (a) operations as illustrated in FIG. 23. In the third embodiment, the cell application operation is repeated a predetermined number of times (e.g., 10 cycles) to produce a desired cell chip or three-dimensional tissue chip. Note that a derivative form of the third embodiment may be configured such that the application unit 60 is only moved vertically during the steps (b) to (c), the application liquid container 80 and the substrate 11 are together moved horizontally, and the application needle is then brought into contact with the application target or the application liquid on the application target to form a liquid droplet spot S on the application target.

In the method for producing a cell chip or three-dimensional tissue chip according to the third embodiment like the above first or second embodiment, the contact application is performed on the application target or the application liquid 10 on the application target while a tiny volume of application liquid 10 is attached to the tip 9a of the application needle 9. A liquid droplet spot S in an application volume of several pL (picoliter) can be applied and formed with high positional precision, such as positional precision of ±15 μm or less and preferably ±3 μm or less. During the cell application operation using the micro-applicator 1 in the third embodiment, a tiny volume of the application liquid 10 attached to the tip 9a of the application needle 9 can be contact-applied, with high precision, onto the application target or the application liquid on the application target. Thus, the application liquid 10 can be applied stably and repeatedly.

Fourth Embodiment

A micro-applicator in a fourth embodiment is not configured such that the application needle penetrates through the application liquid reservoir of the application liquid container, and is configured, like the configuration described in the above second or third embodiment, such that the application liquid, a cell-containing solution, is attached to the tip of the application needle. In the micro-applicator as so configured in the fourth embodiment, the tip of the application needle is subjected to contact application. Accordingly, even when a highly viscous cell-containing gelatinizer is a material, the tip of the application needle is free of clogging and a cell chip or three-dimensional tissue chip formed using a desired application volume can be reliably produced.

Figure 24:
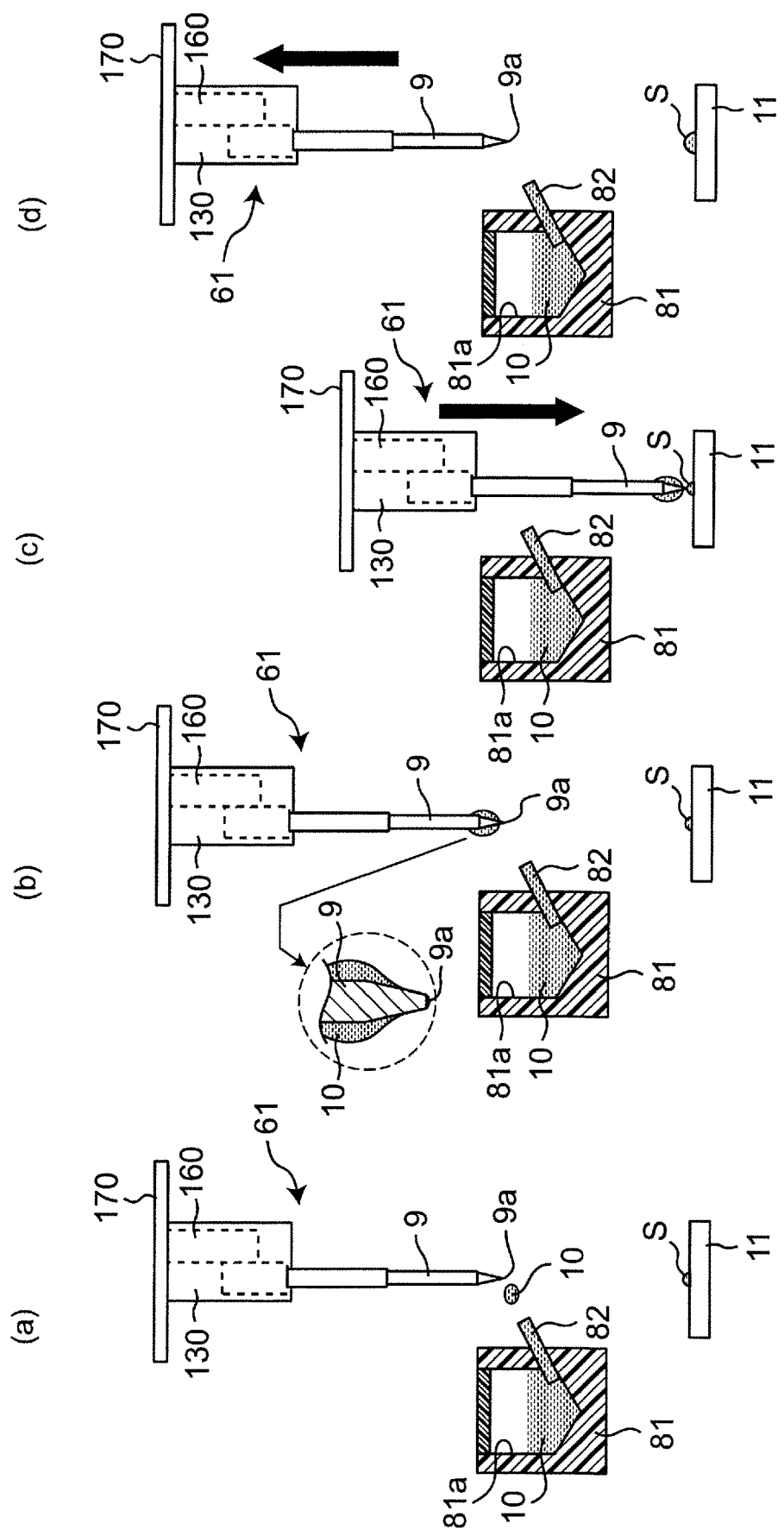
FIG. 24 is diagrams schematically illustrating cell application operation of an application unit in a micro-applicator in a fourth embodiment according to the invention.

FIG. 24 is diagrams schematically illustrating cell application operation of an application unit 61 in the micro-applicator in the fourth embodiment. As shown in FIG. 24, the application unit 61 includes: an application liquid container 81 having an application liquid reservoir 81a in which a prescribed amount of application liquid 10, a cell-containing solution, is stored; a nozzle 82 for jetting the application liquid 10 in the application liquid reservoir 81a toward the tip 9a of the application needle 9; and the application needle holder part 130 holding the application needle 9 having the application liquid 10 attached. Specifically, the application unit 61 in the micro-applicator in the fourth embodiment has, as a component, an inkjet bio-printer and is configured such that a desired volume of the application liquid 10, a cell-containing solution, is attached to the tip 9a of the application needle 9 by jetting from the nozzle 82.

The application needle holder part 130 is provided with the sliding mechanism part 160 that slidably holds the application needle 9 in the top-to-bottom direction (vertical direction). The application needle holder part 130 is detachably provided at a given position on the driving mechanism part 170, and, for instance, is detachable from the driving mechanism part 170 by using magnetic force of a magnet. The driving mechanism part 170 is configured such that the application needle 9 held by the mounted application needle holder part 130 is moved to an application position on an application target (e.g., the substrate 11) and is then subjected to contact application.

[Cell Application Operation]

The cell application operation in the application unit 61, as schematically shown in FIG. 24, will be described. During the cell application operation illustrated in FIG. 24, the application liquid 10, a cell-containing solution, is jetted from the nozzle 82 and a prescribed volume of the application liquid 10 is then attached to the tip 9a of the application needle 9 (see (a) and (b) of FIG. 24). The tip 9a of the application needle 9 having the application liquid 10 attached is moved and then comes into contact with an application target, namely the substrate 11 or the application liquid 10 on the substrate 11 to form a liquid droplet spot S on the substrate 11 (see (c) and (d) of FIG. 24). This cell application operation is repeated a predetermined number of times and the application liquid 10 is subjected to multiple cycles of contact application to produce a desired cell chip or three-dimensional tissue chip on the substrate 11.

(a) of FIG. 24 shows an attachment step during the cell application operation. In this attachment step, the application liquid 10, which is a cell-containing solution stored in the application liquid reservoir 81a of the application liquid container 81, is jetted from the nozzle 82 and then attached to the tip 9a of the application needle 9.

(b) of FIG. 24 shows a transfer step in which the tip 9a of the application needle 9 is moved toward the application target (e.g., the substrate 11). During this transfer step, the application liquid 10 is attached to the tip 9a of the application needle 9 and the surface tension of the application liquid 10 attached causes the tip 9a of the application needle 9 to securely retain a certain volume of application liquid 10.

(c) of FIG. 24 shows an application step of bringing the tip 9a of the application needle 9 into contact with the application target (substrate 11) or the application liquid 10 on the application target to form a new liquid droplet spot S on the application target. The liquid droplet spot S of the application liquid 10 contact-applied at that time corresponds to the volume of application liquid 10 attached to the tip 9a of the application needle 9.

(d) of FIG. 24 shows a state immediately after the application needle 9 is used to apply the application liquid 10 on a surface of the application target (substrate 11) and shows a separation step in which the application needle 9 is lifted from the application target and moves toward a nozzle 82-mediated jetting area. That is, the separation step is in a state in which after the application liquid 10, a cell-containing solution, is subjected to contact application, the tip 9a of the application needle 9 is separated from the application target. This separation step is followed by transition to the attachment step in which the application liquid 10 is jetted from the nozzle 82 toward the tip 9a of the application needle 9 and the application liquid 10 is then attached to the tip 9a of the application needle 9.

As described above, the one cycle of cell application operation includes, in sequence, (a), (b), (c), (d), and (a) operations illustrated in FIG. 24. In the fourth embodiment, the cell application operation is repeated a predetermined number of times (e.g., 10 cycles) to produce a desired cell chip or three-dimensional tissue chip.

In the method for producing a cell chip or three-dimensional tissue chip according to the fourth embodiment as described in the above first to third embodiments, the contact application is performed on the application target or the application liquid 10 on the application target while a tiny volume of application liquid 10 is attached to the tip 9a of the application needle 9. A liquid droplet spot S in an application volume of several pL (picoliter) can be applied and formed with high positional precision, such as positional precision of ±15 μm or less and preferably ±3 μm or less. During the cell application operation using the micro-applicator in the fourth embodiment, a tiny volume of the application liquid 10 attached to the tip 9a of the application needle 9 can be contact-applied, with high precision, onto the application target or the application liquid on the application target. Thus, the application liquid 10 can be applied stably and repeatedly.

Fifth Embodiment

A micro-applicator in a fifth embodiment is not configured such that the application needle penetrates through the application liquid reservoir of the application liquid container, and is configured, like the configuration described in the above second to fourth embodiments, such that the application liquid, a cell-containing solution, is attached to the tip of the application needle. In the micro-applicator as so configured in the fifth embodiment, the tip of the application needle is subjected to contact application. Accordingly, even when a highly viscous cell-containing gelatinizer is a material, the tip of the application needle is free of clogging and a cell chip or three-dimensional tissue chip formed using a desired application volume can be reliably produced.

Figure 25:
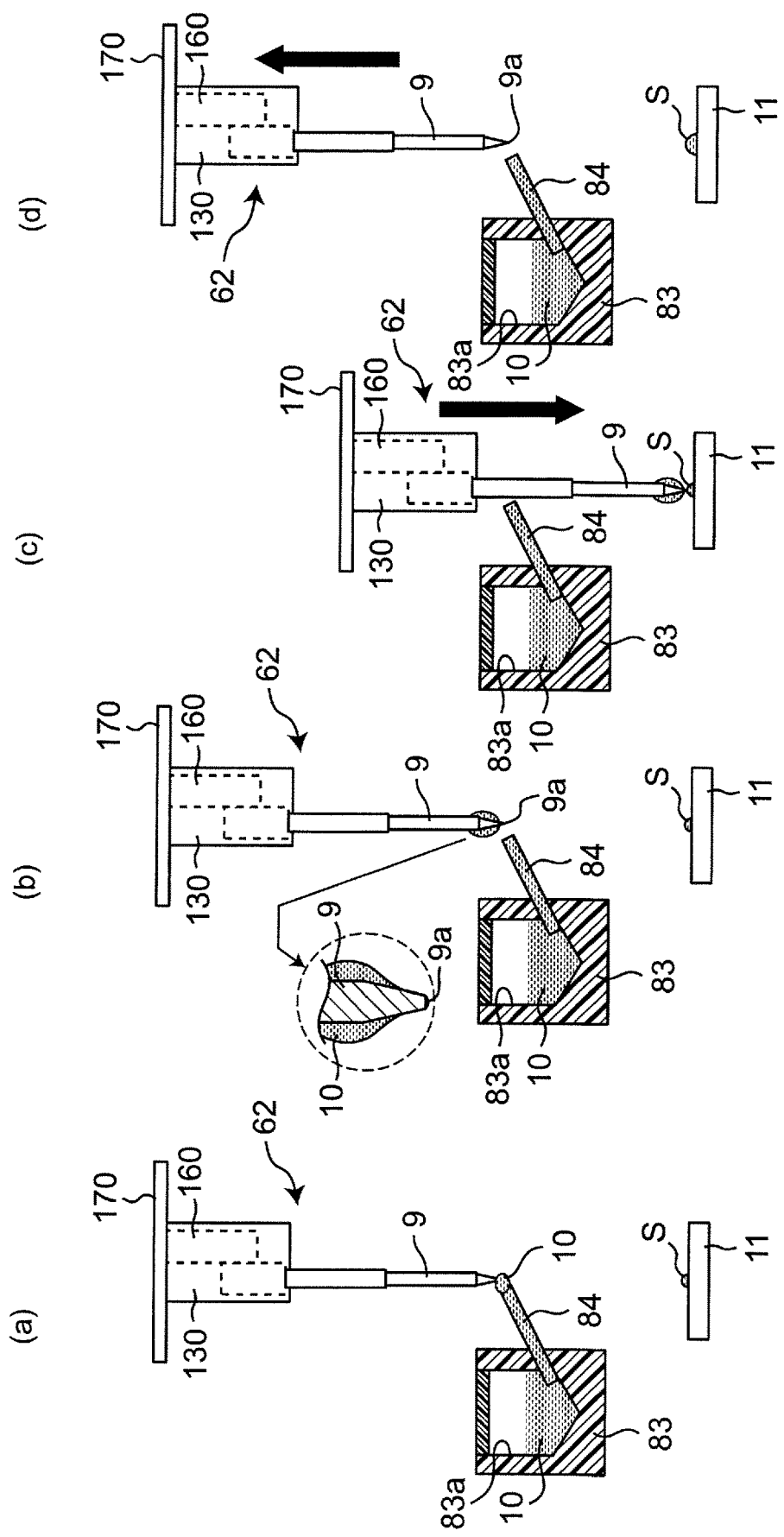
FIG. 25 is diagrams schematically illustrating cell application operation of an application unit in a micro-applicator in a fifth embodiment according to the invention.

FIG. 25 is diagrams schematically illustrating cell application operation of an application unit 62 in the micro-applicator in the fifth embodiment. As shown in FIG. 25, the application unit 62 includes: an application liquid container 83 having an application liquid reservoir 83a in which a prescribed amount of application liquid 10, a cell-containing solution, is stored; a nozzle 84 for attaching the application liquid 10 in the application liquid reservoir 83a to the tip 9a of the application needle 9; and the application needle holder part 130 holding the application needle 9 having the application liquid 10 attached. Specifically, the application unit 62 in the micro-applicator in the fifth embodiment has, as a component, a dispenser-type bio-printer and is configured such that a desired volume of the application liquid 10, a cell-containing solution, is attached to the tip 9a of the application needle 9 by discharging a prescribed volume of the application liquid 10 from the nozzle 84.

The application needle holder part 130 is provided with the sliding mechanism part 160 that slidably holds the application needle 9 in the top-to-bottom direction (vertical direction). The application needle holder part 130 is detachably provided at a given position on the driving mechanism part 170, and, for instance, is detachable from the driving mechanism part 170 by using magnetic force of a magnet. The driving mechanism part 170 is configured such that the application needle 9 held by the mounted application needle holder part 130 is moved to an application position on an application target (e.g., the substrate 11) and is then subjected to contact application.

[Cell Application Operation]

The cell application operation in the application unit 62, as schematically shown in FIG. 25, will be described. During the cell application operation illustrated in FIG. 25, the application liquid 10, a cell-containing solution, is discharged from the nozzle 84 and a prescribed volume of the application liquid 10 is then attached to the tip 9a of the application needle 9 (see (a) and (b) of FIG. 25). The tip 9a of the application needle 9 having the application liquid 10 attached is moved and then comes into contact with an application target, namely the substrate 11 or the application liquid 10 on the substrate 11 to form a liquid droplet spot S on the substrate 11 (see (c) and (d) of FIG. 25). This cell application operation is repeated a predetermined number of times and the application liquid 10 is subjected to multiple cycles of contact application to produce a desired cell chip or three-dimensional tissue chip on the substrate 11.

(a) of FIG. 25 shows an attachment step during the cell application operation. In this attachment step, a prescribed volume of the application liquid 10, which is a cell-containing solution stored in the application liquid reservoir 83a of the application liquid container 83, is discharged from the nozzle 84 and then attached to the tip 9a of the application needle 9.

(b) of FIG. 25 shows a transfer step in which the tip 9a of the application needle 9 is moved toward the application target (e.g., the substrate 11). During this transfer step, the application liquid 10 is attached to the tip 9a of the application needle 9 and the surface tension of the application liquid 10 attached causes the tip 9a of the application needle 9 to securely retain a certain volume of application liquid 10.

(c) of FIG. 25 shows an application step of bringing the tip 9a of the application needle 9 into contact with the application target or the application liquid 10 on the application target to form a new liquid droplet spot S on the application target. The liquid droplet spot S of the application liquid 10 contact-applied at that time corresponds to the volume of application liquid 10 attached to the tip 9a of the application needle 9.

(d) of FIG. 25 shows a state immediately after the application needle 9 is used to apply the application liquid 10 on a surface of the application target and shows a separation step in which the application needle 9 is lifted from the application target and moves toward a nozzle 84-mediated discharging area. That is, the separation step is in a state in which after the application liquid 10, a cell-containing solution, is subjected to contact application, the tip 9a of the application needle 9 is separated from the application target. This separation step is followed by transition to the attachment step in which the application liquid 10 is discharged from the nozzle 84 toward the tip 9a of the application needle 9 and the application liquid 10 is then attached to the tip 9a of the application needle 9.

As described above, the one cycle of cell application operation includes, in sequence, (a), (b), (c), (d), and (a) operations illustrated in FIG. 25. In the fifth embodiment, the cell application operation is repeated a predetermined number of times (e.g., 10 cycles) to produce a desired cell chip or three-dimensional tissue chip.

In the method for producing a cell chip or three-dimensional tissue chip according to the fifth embodiment, as described in the above first to fourth embodiments, the contact application is performed on the application target or the application liquid 10 on the application target while a tiny volume of application liquid 10 is attached to the tip 9a of the application needle 9. A liquid droplet spot S in an application volume of several pL (picoliter) can be applied and formed with high positional precision, such as positional precision of ±15 μm or less and preferably ±3 μm or less. During the cell application operation using the micro-applicator in the fifth embodiment, a tiny volume of the application liquid 10 attached to the tip 9a of the application needle 9 can be contact-applied, with high precision, onto the application target or the application liquid on the application target. Thus, the application liquid 10 can be applied stably and repeatedly.

Examples of the cells that can be used in the invention include: but are not particularly limited to, various primary cells such as fibroblasts, vascular endothelial cells, epithelial cells, smooth muscle cells, cardiomyocytes, gastrointestinal cells, neurons, hepatocytes, renal cells, and/or pancreatic cells; iPS cell-derived differentiated cells; and various cancer cells. As the cells, it is possible to use: cells coated with, for instance, a protein, a sugar chain, nucleic acid, a natural polymer, and/or a synthetic polymer; or cells coated by a coating process(es) or with a known coating agent(s) such as fibrinogen, gelatin, collagen, laminin, elastin, vitronectin, fibrinogen, dextran sulfate, heparan sulfate, polyamino acid, and/or a peptide(s).

Note that to give included cells a stable adhesion/proliferation environment, the cell-containing solution may include: an extracellular matrix component(s) such as fibronectin, gelatin, collagen, laminin, elastin, and/or Matrigel; a cell growth factor(s) such as fibroblast growth factor and/or platelet-derived growth factor; or an additional additive agent(s) such as vascular endothelial cells, lymphatic endothelial cells, and/or various stem cells. In addition, as the gelatinizer, it is possible to include a protein, a sugar chain, a natural polymer, a synthetic polymer, and/or a peptide such as fibrinogen, alginic acid, polyamino acid, polyethylene glycol, and/or a thermally responsive polymer.

As described using the above embodiments and respective experimental examples, the invention provides a novel method for producing a cell chip or three-dimensional tissue chip. Compared to the case of production using a conventional printer with a nozzle, the invention is configured to use the application needle to apply a solution attached to its tip surface. Thus, the solution is not clogged and the resolution and the formation rate of cell assembly is improved, so that a less sample volume (sample) can be used to definitely produce a highly reliable cell chip or three-dimensional tissue chip. In addition, compared to the case of using conventional printers, the invention enables a cell chip or three-dimensional tissue chip to be produced by applying a highly viscous cell dispersion onto a target. This can suppress evaporation of the cell dispersion after the application, thereby capable of maintaining high cell viability.

Regarding the micro-applicators in the invention, the needle (application needle) having a tiny volume of the application liquid attached to the tip is brought into contact with a target (e.g., a substrate); and a liquid droplet in an application volume of several pL (picoliter) can be applied with high positional precision, such as positional precision of ±15 µm or less and preferably ±3 µm or less. In addition, it is possible to apply a material such as a material with a viscosity of the application liquid of $1 \times 10^5$ mPa·s or lower and preferably from 1 to $1 \times 10^4$ mPa·s. This allows for application of highly viscous cell dispersion. As such, according to the invention, a highly viscous cell dispersion can be precisely applied at a predetermined position relative to a target (e.g., a substrate). This makes it possible to produce a cell chip with a given pattern or a three-dimensional tissue chip on which cells are shaped three-dimensionally. As a result, the produced cell chip or three-dimensional tissue chip can be utilized in the fields of regenerative medicine and drug discovery research such as drug efficacy or safety evaluation screening.

The invention has been described in the embodiments in detail to some extent. However, these configurations are examples and the content disclosed in the embodiments may be modified with respect to specifics of the configurations. The elements in the embodiments of the invention may be replaced by other elements and the combinations and the order thereof may be changed, which can be realized without departing from the scope and the spirit of the invention claimed.

INDUSTRIAL APPLICABILITY

According to the present cell chip, three-dimensional tissue chip, and production method therefor, various highly reliable cell chips and three-dimensional tissue chips can be produced in a large quantity. The invention is therefore critical technology in research on drug discovery and regenerative medicine and is highly industrially applicable.

REFERENCE SIGNS LIST 1 micro-applicator
2 applicator main body
3 display/control unit
4 XY table
5 Z table
6 application unit
7 optical detection unit (CCD camera)
8 application liquid container
8a application liquid reservoir
9 application needle
9a tip
9b protrusion
10 application liquid (cell-containing solution)
11 substrate
12 main body base
13 application needle holder part
14a upper hole
14b lower hole
15 cell
16 sliding mechanism part
17 driving mechanism part
20 cell assembly

The invention claimed is:

1. A method for producing a cell chip or three-dimensional tissue chip, the method comprising:
   an attachment step of attaching a cell-containing solution to a tip of an application needle;
   a transfer step of moving the cell-containing solution-attached tip of the application needle closer to an application target;
   an application step of bringing the cell-containing solution attached to the tip of the application needle into contact with the application target or into contact with a second cell-containing solution that has been previously applied on the application target, thereby subjecting the cell-containing solution attached to the tip of the application needle to contact application; and
   a separation step of, after the cell-containing solution is subjected to the contact application, making the tip of the application needle apart from the application target,
   wherein the tip of the application needle comprises a flat surface perpendicular to a transfer direction of the application needle during the application step.

2. The method for producing a cell chip or three-dimensional tissue chip according to claim 1, wherein the tip of the application needle is configured to move in a vertical direction during the application step.

3. The method for producing a cell chip or three-dimensional tissue chip according to claim 1, wherein a cell having a coated cell surface is used as a cell in the cell-containing solution.

4. A method for producing a cell chip or three-dimensional tissue chip, the method comprising:
   an attachment step of attaching a cell-containing solution to a tip of an application needle;
   a transfer step of moving the cell-containing solution-attached tip of the application needle closer to an application target;
   an application step of bringing the cell-containing solution attached to the tip of the application needle into contact with the application target or into contact with a second cell-containing solution that has been previously applied on the application target, thereby subjecting the cell-containing solution attached to the tip of the application needle to contact application; and a separation step of, after the cell-containing solution is subjected to the contact application, making the tip of the application needle apart from the application target,
wherein multiple cycles of cell application operation are repeated and wherein one cycle of the cell application operation includes the attachment step, the transfer step, the application step, and the separation step, and
wherein the cell application operation is carried out using a material in which viscosity of the cell-containing solution is $1 \times 10^5$ mPa·s or less.

5. The method for producing a cell chip or three-dimensional tissue chip according to claim 4, wherein the one cycle of the cell application operation is conducted in 0.5 sec or less.

6. The method for producing a cell chip or three-dimensional tissue chip according to claim 4, wherein a liquid droplet spot obtained by the one cycle of the cell application operation is formed on the application target with positional precision of ±15 μm or less.

7. The method for producing a cell chip or three-dimensional tissue chip according to claim 4, wherein a liquid droplet spot obtained by the one cycle of the cell application operation is formed on the application target with positional precision of ±3 μm or less.

8. The method for producing a cell chip or three-dimensional tissue chip according to claim 4, wherein multiple cycles of the cell application operation are repeated while a stop position of the tip of the application needle in the application step is shifted upward with respect to a certain position relative to the application target by a given distance every cycle of the cell application operation.

9. The method for producing a cell chip or three-dimensional tissue chip according to claim 4, wherein the cell application operation is carried out using a material in which viscosity of the cell-containing solution is $1 \times 10^4$ mPa·s or less.

10. A method for producing a cell chip or three-dimensional tissue chip by using a micro-applicator provided with an application unit including an application liquid container having an application liquid reservoir for storing a cell-containing solution in a prescribed amount and an application needle allowing for penetration through the application liquid reservoir having the cell-containing solution stored, the method comprising:
 a waiting step of making a tip of the application needle dipped dip into the cell-containing solution having been charged in the application liquid reservoir;
 a descending step of making the tip of the application needle penetrate through the application liquid reservoir to move downward the cell-containing solution-attached tip of the application needle;
 an application step of bringing the cell-containing solution-attached tip of the application needle into contact with an application target, thereby applying the cell-containing solution to the application target to form a liquid droplet spot; and
 a holding step of lifting the tip of the application needle and holding the tip of the application needle in the application liquid reservoir.

11. The method for producing a cell chip or three-dimensional tissue chip according to claim 10, wherein multiple cycles of cell application operation are repeated and wherein one cycle of the cell application operation includes the waiting step, the descending step, the application step, and the holding step performed with respect to certain positions relative to the application target.

12. The method for producing a cell chip or three-dimensional tissue chip according to claim 11, wherein the one cycle of the cell application operation is conducted in 0.5 sec or less.

13. The method for producing a cell chip or three-dimensional tissue chip according to claim 11, wherein the cell application operation is carried out using a material in which viscosity of the cell-containing solution is $1 \times 10^5$ mPa·s or less.

14. The method for producing a cell chip or three-dimensional tissue chip according to claim 13, wherein the cell application operation is carried out using a material in which viscosity of the cell-containing solution is $1 \times 10^4$ mPa·s or less.

15. The method for producing a cell chip or three-dimensional tissue chip according to claim 11, wherein a liquid droplet spot obtained by the one cycle of the cell application operation is formed on the application target with positional precision of ±15 μm or less.

16. The method for producing a cell chip or three-dimensional tissue chip according to any one of claim 11, wherein the liquid droplet spot obtained by the one cycle of the cell application operation is formed on the application target with positional precision of ±3 μm or less.

17. The method for producing a cell chip or three-dimensional tissue chip according to claim 11, wherein multiple cycles of the cell application operation are repeated while a stop position of the tip of the application needle in the application step is shifted upward with respect to a certain position relative to the application target by a given distance every cycle of the cell application operation.

18. The method for producing a cell chip or three-dimensional tissue chip according to claim 10, wherein the application unit comprises a sliding mechanism part for slidably holding the application needle.

19. The method for producing a cell chip or three-dimensional tissue chip according to claim 18, wherein the sliding mechanism part has a mechanism for absorbing a shock when the tip of the application needle comes into contact with the application target.

20. The method for producing a cell chip or three-dimensional tissue chip according to claim 10, wherein the tip of the application needle is configured to move in a vertical direction during the application step.

21. The method for producing a cell chip or three-dimensional tissue chip according to claim 10, wherein the tip of the application needle comprises a flat surface perpendicular to a transfer direction of the application needle during the application step.

22. The method for producing a cell chip or three-dimensional tissue chip according to claim 10, wherein the tip of the application needle comprises a recessed surface.

23. The method for producing a cell chip or three-dimensional tissue chip claim 10, wherein a cell having a coated cell surface is used as a cell in the cell-containing solution.

* * * * *